United States Patent
McDermott et al.

(10) Patent No.: US 9,701,177 B2
(45) Date of Patent: Jul. 11, 2017

(54) CERAMIC COATED AUTOMOTIVE HEAT EXCHANGER COMPONENTS

(75) Inventors: Chris McDermott, Portage, MI (US); Jason Amoss, Battle Creek, MI (US); Rajaram Shembekar, Portage, MI (US); Shawn E. Dolan, Sterling Heights, MI (US)

(73) Assignees: Henkel AG & Co. KGaA, Duesseldorf (DE); DENSO Manufacturing Michigan, Inc., East Lansing, MI (US)

( * ) Notice: Subject to any disclaimer, the term of this patent is extended or adjusted under 35 U.S.C. 154(b) by 1346 days.

(21) Appl. No.: 12/417,433

(22) Filed: Apr. 2, 2009

(65) Prior Publication Data

US 2010/0252241 A1 Oct. 7, 2010

(51) Int. Cl.
| | |
|---|---|
| *F28F 13/18* | (2006.01) |
| *B32B 7/02* | (2006.01) |
| *H01F 3/00* | (2006.01) |
| *B60H 3/00* | (2006.01) |
| *C04B 35/622* | (2006.01) |
| *C25D 11/04* | (2006.01) |
| *C25D 11/06* | (2006.01) |
| *C25D 11/24* | (2006.01) |
| *C25D 11/36* | (2006.01) |
| *F28F 19/02* | (2006.01) |
| *F28F 21/08* | (2006.01) |

(Continued)

(52) U.S. Cl.
CPC ..... *B60H 3/0085* (2013.01); *C04B 35/62222* (2013.01); *C23C 28/042* (2013.01); *C25D 11/024* (2013.01); *C25D 11/026* (2013.01); *C25D 11/04* (2013.01); *C25D 11/06* (2013.01); *C25D 11/24* (2013.01); *C25D 11/36* (2013.01); *F28F 19/02* (2013.01); *F28F 21/084* (2013.01); *A61L 9/205* (2013.01); *F28F 2265/20* (2013.01); *Y02T 50/67* (2013.01)

(58) Field of Classification Search
CPC ..... B60H 3/0085; A61L 9/205; F28F 2265/20
USPC .................. 165/133; 428/212, 566
See application file for complete search history.

(56) References Cited

U.S. PATENT DOCUMENTS

| | | |
|---|---|---|
| 2,081,121 A | 5/1937 | Stareck |
| 2,231,373 A | 2/1941 | Schenk |
| (Continued) | | |

FOREIGN PATENT DOCUMENTS

| | | |
|---|---|---|
| CA | 2474367 A1 | 1/2006 |
| CA | 2479032 A1 | 3/2006 |
| (Continued) | | |

OTHER PUBLICATIONS

Arctander, Steffan, "Perfume and Flavor Chemicals", Aroma Chemicals, vol. 1 & 2, published 1969 by the author.

(Continued)

*Primary Examiner* — Henry Crenshaw
(74) *Attorney, Agent, or Firm* — Mary K. Cameron; J. Blair Miller

(57) ABSTRACT

A ceramic coated heat exchanger component and method for making the ceramic coated heat exchanger component by creating porous metal oxide coatings on an aluminum surface of the heat exchanger component by plasma electrochemical deposition of a metal oxide on the aluminum surface and layering an odor neutralization agent on the porous metal oxide ceramic coatings to form an odor remediation ceramic coating on the heat exchanger.

9 Claims, 1 Drawing Sheet

(51) Int. Cl.
  *C25D 11/02* (2006.01)
  *C23C 28/04* (2006.01)
  *A61L 9/20* (2006.01)

(56) References Cited

U.S. PATENT DOCUMENTS

| | | | |
|---|---|---|---|
| 2,275,223 A | 3/1942 | Hardoen | |
| 2,305,669 A | 12/1942 | Budiloff et al. | |
| 2,438,877 A | 3/1948 | Spruance, Jr. | |
| 2,573,229 A | 10/1951 | Stern | |
| 2,858,285 A | 10/1958 | Johnson | |
| 2,880,148 A | 3/1959 | Evangelides | |
| 2,901,409 A | 8/1959 | De Long | |
| 2,926,125 A | 2/1960 | Currah et al. | |
| 3,343,930 A * | 9/1967 | Borzillo et al. | 428/653 |
| 3,345,276 A | 10/1967 | Munroe | |
| 3,426,011 A | 2/1969 | Parmerter et al. | |
| 3,453,257 A | 7/1969 | Parmerter et al. | |
| 3,453,258 A | 7/1969 | Parmerter et al. | |
| 3,453,259 A | 7/1969 | Parmerter et al. | |
| 3,453,260 A | 7/1969 | Parmerter et al. | |
| 3,459,731 A | 8/1969 | Gramera et al. | |
| 3,524,799 A | 8/1970 | Dale | |
| 3,553,191 A | 1/1971 | Parmerter et al. | |
| 3,565,887 A | 2/1971 | Parmerter et al. | |
| 3,620,940 A | 11/1971 | Wick | |
| 3,681,180 A | 8/1972 | Kent | |
| 3,729,391 A | 4/1973 | Houghton et al. | |
| 3,778,315 A | 12/1973 | Booker et al. | |
| 3,824,159 A | 7/1974 | Wehrmann | |
| 3,864,224 A * | 2/1975 | Cotton | C25B 1/00 205/322 |
| 3,865,560 A | 2/1975 | Sabetay | |
| 3,945,899 A | 3/1976 | Nikaido et al. | |
| 3,950,240 A | 4/1976 | Cookfair et al. | |
| 3,956,080 A | 5/1976 | Hradcovsky et al. | |
| 3,960,676 A * | 6/1976 | Miyosawa | C25D 11/00 204/486 |
| 3,996,115 A * | 12/1976 | Kessler | C23C 22/00 205/316 |
| 4,082,626 A | 4/1978 | Hradcovsky | |
| 4,094,750 A | 6/1978 | Mackey | |
| RE29,739 E | 8/1978 | Kessler | |
| 4,110,147 A | 8/1978 | Grunwald et al. | |
| 4,113,598 A | 9/1978 | Jozwiak, Jr. et al. | |
| 4,145,263 A | 3/1979 | Tsutsui et al. | |
| 4,166,777 A | 9/1979 | Casson, Jr. et al. | |
| 4,184,926 A | 1/1980 | Kozak | |
| 4,188,270 A | 2/1980 | Kataoka | |
| 4,200,475 A | 4/1980 | Kasahara et al. | |
| 4,227,976 A | 10/1980 | Menke | |
| 4,298,661 A | 11/1981 | Ikeno et al. | |
| 4,370,538 A | 1/1983 | Browning | |
| 4,383,897 A | 5/1983 | Gillich et al. | |
| 4,399,021 A | 8/1983 | Gillich et al. | |
| 4,401,489 A | 8/1983 | Arai et al. | |
| 4,439,287 A | 3/1984 | Birkle et al. | |
| 4,448,647 A | 5/1984 | Gillich et al. | |
| 4,452,674 A | 6/1984 | Gillech et al. | |
| 4,455,201 A | 6/1984 | Birkle et al. | |
| 4,456,663 A | 6/1984 | Leonard | |
| 4,473,110 A | 9/1984 | Zawierucha | |
| 4,511,632 A * | 4/1985 | Toma et al. | 428/654 |
| 4,511,633 A | 4/1985 | Bruno et al. | |
| 4,535,152 A | 8/1985 | Szejtli et al. | |
| 4,551,211 A | 11/1985 | Kobayashi et al. | |
| 4,578,156 A | 3/1986 | Plazter | |
| 4,579,786 A | 4/1986 | Nakakouji et al. | |
| 4,616,008 A | 10/1986 | Hirai et al. | |
| 4,620,904 A | 11/1986 | Kozak | |
| 4,638,058 A | 1/1987 | Brandt et al. | |
| 4,659,440 A | 4/1987 | Hradcovsky | |
| 4,668,347 A | 5/1987 | Habermann et al. | |
| 4,678,598 A | 7/1987 | Ogino et al. | |
| 4,705,731 A | 11/1987 | Saitoh et al. | |
| 4,744,872 A | 5/1988 | Kobayashi et al. | |
| 4,746,734 A | 5/1988 | Tsuchiyama et al. | |
| 4,775,600 A | 10/1988 | Adaniya et al. | |
| 4,786,336 A | 11/1988 | Schoener et al. | |
| 4,839,002 A | 6/1989 | Pernick et al. | |
| 4,859,288 A | 8/1989 | Furneaux et al. | |
| 4,869,789 A | 9/1989 | Kurze et al. | |
| 4,869,936 A | 9/1989 | Moskowitz et al. | |
| 4,882,014 A | 11/1989 | Coyle et al. | |
| 4,976,830 A | 12/1990 | Schmeling et al. | |
| 4,978,432 A | 12/1990 | Schmeling et al. | |
| 5,032,129 A | 7/1991 | Kurze et al. | |
| 5,087,645 A | 2/1992 | Kojima et al. | |
| 5,100,486 A | 3/1992 | Krikorian et al. | |
| 5,102,746 A | 4/1992 | Shindou et al. | |
| 5,201,119 A * | 4/1993 | Mizuno et al. | 29/890.047 |
| 5,221,576 A | 6/1993 | Bosc et al. | |
| H1207 H | 7/1993 | Smith | |
| 5,240,589 A | 8/1993 | Bartak et al. | |
| 5,264,113 A | 11/1993 | Bartak et al. | |
| 5,266,412 A | 11/1993 | Bartak et al. | |
| 5,275,713 A | 1/1994 | Hradcovsky | |
| 5,283,131 A | 2/1994 | Mori et al. | |
| 5,302,414 A | 4/1994 | Alkhimov et al. | |
| 5,314,334 A | 5/1994 | Panzera et al. | |
| 5,356,490 A | 10/1994 | Dolan et al. | |
| 5,385,662 A | 1/1995 | Kurze et al. | |
| 5,441,580 A | 8/1995 | Tomlinson | |
| 5,451,271 A | 9/1995 | Yoshida et al. | |
| 5,470,664 A | 11/1995 | Bartak et al. | |
| 5,478,237 A | 12/1995 | Ishizawa | |
| 5,583,704 A | 12/1996 | Fujii | |
| 5,700,366 A | 12/1997 | Steblianko et al. | |
| 5,711,071 A * | 1/1998 | Fromson | B01D 53/885 29/890 |
| 5,759,251 A * | 6/1998 | Nakamura et al. | 106/286.4 |
| 5,775,892 A | 7/1998 | Miyasaka et al. | |
| 5,792,335 A | 8/1998 | Barton | |
| 5,811,194 A | 9/1998 | Kurze et al. | |
| 5,837,117 A | 11/1998 | Allegret | |
| 5,899,082 A | 5/1999 | Stein et al. | |
| 5,945,035 A | 8/1999 | Vogt et al. | |
| 5,958,604 A | 9/1999 | Riabkov et al. | |
| 5,981,084 A | 11/1999 | Riabkov et al. | |
| 6,030,526 A * | 2/2000 | Porter | 210/198.1 |
| 6,059,897 A | 5/2000 | Koerner et al. | |
| 6,068,890 A | 5/2000 | Kaumle et al. | |
| 6,082,444 A | 7/2000 | Harada et al. | |
| 6,090,490 A | 7/2000 | Mokerji | |
| 6,127,052 A | 10/2000 | Tomari | |
| 6,142,222 A * | 11/2000 | Kang et al. | 165/148 |
| 6,153,080 A | 11/2000 | Heimann et al. | |
| 6,159,618 A | 12/2000 | Danroc et al. | |
| 6,165,630 A | 12/2000 | Gehlhaar et al. | |
| 6,180,548 B1 * | 1/2001 | Taoda et al. | 501/137 |
| 6,197,178 B1 | 3/2001 | Patel et al. | |
| 6,245,436 B1 | 6/2001 | Boyle | |
| 6,280,598 B1 | 8/2001 | Barton et al. | |
| 6,335,099 B1 | 1/2002 | Higuchi et al. | |
| 6,372,115 B1 | 4/2002 | Miyasaka et al. | |
| 6,595,341 B1 * | 7/2003 | Venz | 192/85.53 |
| 6,599,618 B1 * | 7/2003 | Simmon, Jr. | 428/212 |
| 6,797,147 B2 * | 9/2004 | Dolan | 205/316 |
| 6,803,023 B1 * | 10/2004 | Ohmori et al. | 422/177 |
| 6,840,051 B1 | 1/2005 | Stein | |
| 6,861,101 B1 | 3/2005 | Kowalsky et al. | |
| 6,863,990 B2 | 3/2005 | Wu et al. | |
| 6,869,703 B1 | 3/2005 | Spitsberg et al. | |
| 6,875,529 B1 | 4/2005 | Spitsberg et al. | |
| 6,896,970 B2 | 5/2005 | Mayzel | |
| 6,916,414 B2 * | 7/2005 | Dolan | 205/316 |
| 7,353,863 B2 | 4/2008 | Kobayashi et al. | |
| 7,452,454 B2 | 11/2008 | Dolan | |
| 7,569,132 B2 | 8/2009 | Dolan | |
| 7,578,921 B2 | 8/2009 | Dolan | |
| 7,820,300 B2 | 10/2010 | Dolan | |
| 2001/0007714 A1 | 7/2001 | Gaboury et al. | |
| 2002/0040742 A1 * | 4/2002 | Kojima | B05D 7/51 148/240 |

(56) References Cited

U.S. PATENT DOCUMENTS

| | | | |
|---|---|---|---|
| 2003/0000847 A1 | 1/2003 | Ostrovsky | |
| 2003/0070935 A1 | 4/2003 | Dolan | |
| 2003/0075453 A1 | 4/2003 | Dolan | |
| 2003/0118664 A1* | 6/2003 | Trogolo et al. | 424/618 |
| 2003/0150524 A1 | 8/2003 | Wichelhaus et al. | |
| 2004/0081881 A1 | 4/2004 | Vyas et al. | |
| 2004/0099535 A1 | 5/2004 | Schweinsberg et al. | |
| 2004/0129294 A1* | 7/2004 | Takamasa et al. | 134/1 |
| 2004/0202890 A1 | 10/2004 | Kutilek et al. | |
| 2004/0245496 A1* | 12/2004 | Taoda | 252/186.1 |
| 2005/0115840 A1* | 6/2005 | Dolan | 205/324 |
| 2005/0175798 A1 | 8/2005 | Kurokawa et al. | |
| 2006/0099397 A1* | 5/2006 | Thierauf et al. | 428/312.2 |
| 2006/0123558 A1* | 6/2006 | Li et al. | 8/115.51 |
| 2006/0188741 A1* | 8/2006 | Date et al. | 428/566 |
| 2006/0196644 A1 | 9/2006 | Boger et al. | |
| 2007/0041893 A1* | 2/2007 | Holladay et al. | 423/648.1 |
| 2007/0125520 A1* | 6/2007 | Nutsos | 165/95 |
| 2007/0144914 A1* | 6/2007 | Schweinsberg et al. | 205/318 |
| 2008/0014393 A1* | 1/2008 | Denome et al. | 428/35.7 |
| 2008/0038144 A1* | 2/2008 | Maziasz et al. | 420/45 |
| 2008/0248214 A1* | 10/2008 | Nie et al. | 427/534 |
| 2009/0010958 A1 | 1/2009 | Pinney | |
| 2009/0098373 A1 | 4/2009 | Dolan | |
| 2009/0162563 A1 | 6/2009 | Schweinsberg et al. | |
| 2009/0258242 A1 | 10/2009 | Dolan | |
| 2010/0252241 A1 | 10/2010 | McDermott et al. | |

FOREIGN PATENT DOCUMENTS

| | | | |
|---|---|---|---|
| CA | 2585278 A1 | 5/2006 | |
| CA | 2585283 A1 | 5/2006 | |
| CA | 2556869 A1 | 2/2008 | |
| CN | 1392284 A | 1/2003 | |
| DE | 3516411 A1 | 11/1986 | |
| DE | 289054 A5 | 4/1991 | |
| DE | 289065 A5 | 4/1991 | |
| DE | 4104847 A1 | 8/1992 | |
| DE | 19750128 A1 | 5/1999 | |
| EP | 0259657 A1 | 3/1988 | |
| EP | 0594374 A1 | 4/1994 | |
| EP | 0823496 A1 | 2/1998 | |
| EP | 0978576 A1 | 2/2000 | |
| EP | 1002644 A2 | 5/2000 | |
| EP | 1154042 A1 | 11/2001 | |
| EP | 0780494 B1 | 11/2002 | |
| EP | 1407832 A2 | 4/2004 | |
| FR | 2549092 A1 | 1/1985 | |
| FR | 2657090 A1 | 7/1991 | |
| GB | 294237 A | 9/1929 | |
| GB | 493935 A | 10/1938 | |
| GB | 1051665 A | 12/1966 | |
| GB | 1319912 A | 6/1973 | |
| GB | 2158842 A | 11/1985 | |
| GB | 2343681 A | 5/2000 | |
| JP | 5311133 A | 2/1978 | |
| JP | 56152994 A | 11/1981 | |
| JP | 57057888 A | 4/1982 | |
| JP | 57060098 A | 4/1982 | |
| JP | 57131391 A | 8/1982 | |
| JP | 58001093 A | 1/1983 | |
| JP | 59016994 A | 1/1984 | |
| JP | 63087716 A | 4/1988 | |
| JP | 63100194 A | 5/1988 | |
| JP | 4308093 A | 10/1992 | |
| JP | 5287587 A | 11/1993 | |
| JP | 6173034 A | 6/1994 | |
| JP | 06173034 A | 6/1994 | |
| JP | 9503824 T | 4/1997 | |
| JP | 9176894 A | 7/1997 | |
| JP | 10018082 A | 1/1998 | |
| JP | 11043799 A | 2/1999 | |
| JP | 11324879 A | 11/1999 | |
| JP | 2000153390 A * | 6/2000 | B23K 35/28 |
| JP | 2000248398 A | 9/2000 | |
| JP | 2000273656 A | 10/2000 | |
| JP | 3132133 B2 | 2/2001 | |
| JP | 2001201288 * | 7/2001 | F28F 13/18 |
| JP | 2001201288 A * | 7/2001 | F28F 13/18 |
| JP | 2001343090 A | 12/2001 | |
| JP | 2003074932 A * | 3/2003 | F24F 7/06 |
| JP | 2003279060 A | 10/2003 | |
| JP | 2004052000 A | 2/2004 | |
| JP | 2004092931 A | 3/2004 | |
| JP | 2004190121 A | 7/2004 | |
| JP | 2005214469 A | 8/2005 | |
| JP | 3120756 U | 3/2006 | |
| JP | 2008518096 A | 5/2008 | |
| JP | 2008202931 A | 9/2008 | |
| JP | 2008253895 A | 10/2008 | |
| JP | 200930894 A | 2/2009 | |
| RU | 2049162 C1 | 11/1995 | |
| RU | 2112087 C1 | 5/1998 | |
| RU | 2213166 C2 | 9/2003 | |
| SU | 617493 A1 | 7/1978 | |
| WO | 9214868 A1 | 9/1992 | |
| WO | 9842892 A1 | 10/1998 | |
| WO | 9842895 A1 | 10/1998 | |
| WO | 9902759 A1 | 1/1999 | |
| WO | 0003069 A1 | 1/2000 | |
| WO | 0228838 A2 | 4/2002 | |
| WO | 03029528 A1 | 4/2003 | |
| WO | 03029529 A1 | 4/2003 | |
| WO | 2006047500 A2 | 5/2006 | |

OTHER PUBLICATIONS

International Search Report dated Nov. 30, 2010, International application PCT/US2010/029608.

Written Opinion dated Nov. 30, 2010, International application PCT/US2010/029608.

Zozulin, Alex J.; Technology Applications Group, Inc., "A Chromate-free Anodize Process for Magnesium Alloys: A Coating With Superior Characteristics", pp. 47-63.

Zozulin, Alex J. et al; Technology Applications Group, Inc., et al , "Anodized Coatings for Magnesium Alloys", Metal Finishing, Mar. 1994, pp. 39-44.

IBM Technical Disclosure Bulletin, "Forming Protective Coatings on Magnesium Alloys", Dec. 1967, p. 862.

Barton, et al; "The Effect of Electrolyte on the Anodized Finish of a Magnesium Alloy"; Plating & Surface Finishing, vol. 5, 1995, pp. 138-141.

Jakobson, et al; "Magnesium Anodizing", 85th American Electroplaters and Surface Finishers Society, Jun. 1998, pp. 541-550.

International Search Report for PCT/US2010/029608 mailed Nov. 30, 2010.

Yerokhin, A.L., et al, "Plasma Electrolysis for Surface Engineering", Surface and Coatings Technology 122, 1999, pp. 73-93.

Galvanotechnik, "Plasmachemische Oxicfationsverfahren Teil 1: Historie und Verfahrensgrundlagen", (Apr. 2003), pp. 816-823.

Galvanotechnik, "Plasmachemische Oxicfationsverfahren Teil 2: Apparative Voraussetzungen", (Jun. 2003), pp. 1374-1382.

Galvanotechnik, "Plasmachemische Oxicfationsverfahren Teil 3: Neue Schichtsysteme, aussergewoehnliche Substratmaterialien und deren gegenwaertige und Zukuenftige Anwendungsfelder," (Jul. 2003), pp. 1634-1645.

Sworn Declaration of Dr. Peter Kurze dated Jul. 5, 2000, submitted in connection with PCT Publication WO 96/28591 of Magnesium Technology Limited.

Zhou, Y. et al, "Electrochemical Deposition and Microstructure of Copper (I) Oxide Films", Scripta Materials, vol. 38, No. 11, pp. 1731-1738 (1998).

Yoshimura et al, "Recent developments in soft, solution processing: one step fabrication of functional double oxide films by hydrothermal-electrochemical methods", Journal of Materials Chemistry, vol. 9, pp. 77-82 (1999).

Zhang, Yong-gang et al, "Pore structure of activated alumina carrier", Industrial Catalysis, vol. 8, No. 2., Nov. 2000 - with English abstract.

* cited by examiner

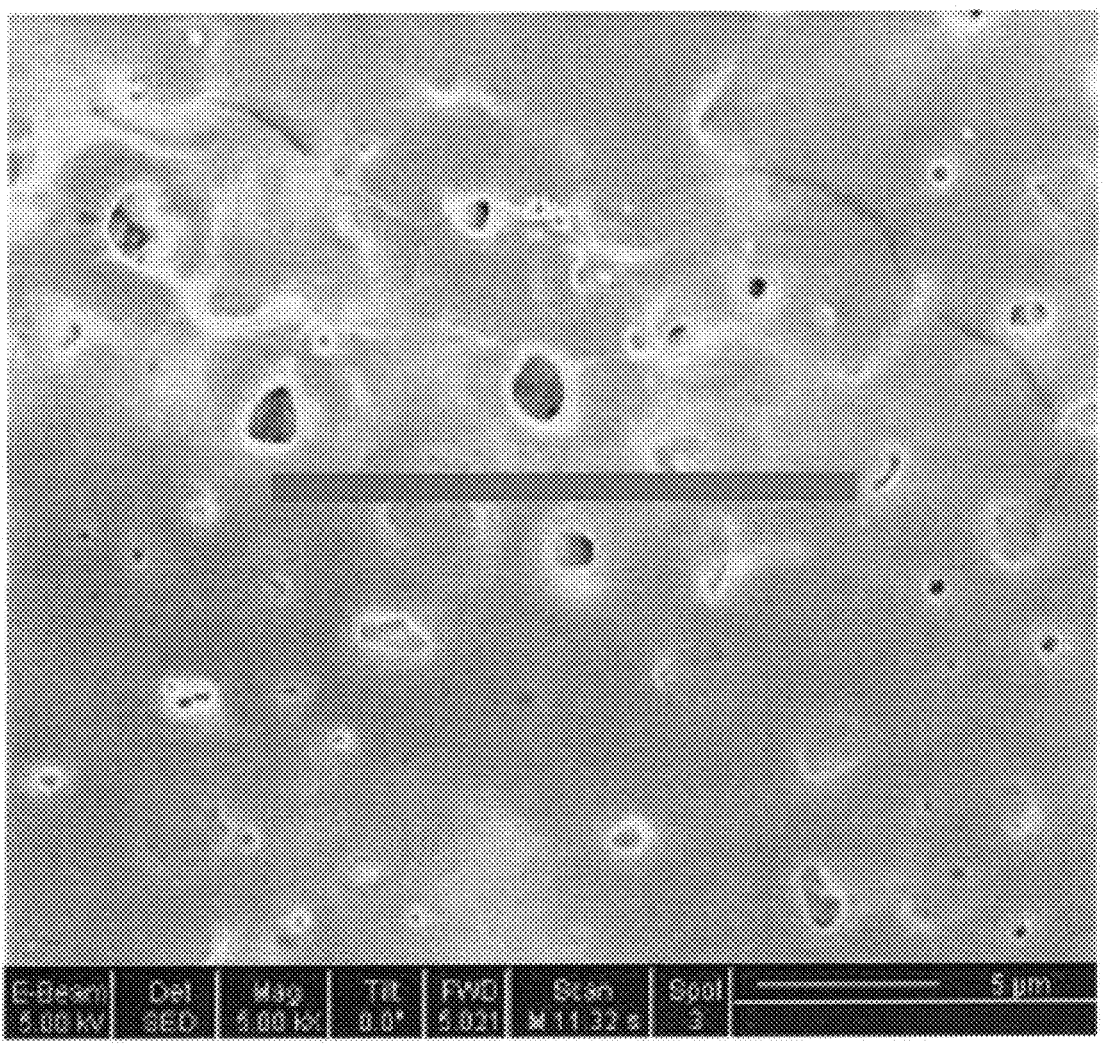

CERAMIC COATED AUTOMOTIVE HEAT EXCHANGER COMPONENTS

FIELD

The present technology relates to methods for coating automotive heat exchanger components with a metal oxide ceramic coating using an electrochemical deposition method and ceramic coated automotive heat exchanger components produced therefrom.

BACKGROUND

This section provides background information related to the present disclosure which is not necessarily prior art.

Conventional heat exchangers having heat-exchanging tubes and fins comprising aluminum or an aluminum alloy are mostly designed so that the surface areas of heat-radiating portions and cooling portions are as large as possible, to obtain excellent heat-radiation or cooling effects in a limited space. Therefore, the gaps between the fins are very small. Also, to decrease air resistance of the heat exchanger to as low as possible, the fins are notched. The notched fin is referred to as a fin louver.

When the above-mentioned heat exchangers are used for cooling, the moisture contained in air is condensed on the surface of the heat exchanger to form water droplets which fill the gaps between the fins to increase the air resistance of the heat exchanger, and thus the heat-exchanging efficiency of the heat-exchanger is decreased. Also, the condensed water drops cause corrosion of aluminum or aluminum alloy in the heat exchanger, and thus a fine white powder of aluminum oxide is generated on the fin surfaces. To prevent the blockage of the heat exchanger by the water drops remaining in the gaps between the fins, treatment methods for imparting a high hydrophilicity to the fin surfaces and for enhancing the water-wetting property of the fin surfaces have been developed.

As a surface treatment for a purpose of preventing a corrosion of the aluminum or aluminum alloy heat exchanger, a chromic acid-chromate chemical conversion treatment, a phosphoric acid-chromate chemical conversion treatment, and non-chromate chemical conversion treatments are known. The chromic acid-chromate chemical conversion treatment was practically utilized from about 1950 and is still widely used for the fin materials of heat exchangers, etc. This chemical conversion treatment liquid contains, as main components, chromic acid ($CrO_3$) and hydrofluoric acid (HF), and further an accelerator, and can form a chemical conversion coating containing a small amount of hexavalent chromium. The phosphoric acid-chromate chemical conversion treatment is based on the invention of U.S. Pat. No. 2,438,877 and the treatment liquid thereof comprises chromic acid ($CrO_3$), phosphoric acid ($H_3PO_4$) and hydrofluoric acid (HF). The resultant chemical conversion coating contains, as a principal component, hydrated chromium phosphate ($CrPO_4 \cdot 4H_2O$).

This process is, however, disadvantageous in that the coating procedure causes a waste liquid containing hexavalent chromium ($Cr^{6+}$) to be discharged. Since the chromate type surface treatments use an aqueous treatment liquid containing harmful hexavalent chromium, there is a strong demand for a new treatment liquid containing no hexavalent chromium, to prevent environmental pollution. Also, since the above-mentioned waste liquid is not allowed to be discharged without a hexavalent chromium-removing treatment, the waste liquid must be treated by a treatment apparatus using treatment reagents which causes the resultant product to be expensive.

Vehicles often accumulate odors inside their cabins during their lifetime of use. Such odors can be caused in a variety of ways and by a variety of sources. For example, objects left inside the vehicle, volatile organic compounds (VOCs) from the cabin interior materials, activities such as smoking and eating and the accumulation of dust and other pollutants suspended in the air can all contribute to the accumulation of odors. Eventually odors inside a vehicle become annoying and in some cases they may become a health risk if the source of odor involves bacteria, mold (fungi) or other microorganisms.

One location for the growth and/or accumulation of hidden pollutants is in the interior of the air conditioning system. Typical air conditioning units include a chamber, where the refrigerant serpentine, also known as evaporator core, is embedded. Under normal operating conditions of a properly functioning air conditioning system, the serpentine condenses the moisture coming into the chamber due to the interaction between temperature, the existing dew point, and the relative humidity inside and outside the vehicle. In this process, the air entering the system contacts the cold interior parts of the system which retain and condense the humidity from the air. The cooler drier air comforts passengers once it exits the system, vents, and enters the vehicle cabin.

Cigarette smoke generated in the interior of an automobile will be channeled eventually through the automobile's heat exchanger system. Often, the odor remains resilient to removal, depreciates the value of the automobile and causes irritation to passengers.

In addition, some of the pollutants pass through the system and can become deposited over the interior surfaces of the cabin. The accumulated particles on the moist surfaces of the evaporator provide an environment in which microorganisms can grow, particularly in the absence of UV light from the sun. The growth of microbial pollutants inside the evaporator further increases the amount of pollutants and odors that can enter the cabin in the airflow created by the blower.

The mold can generate spores that can become suspended in the air inside the cabin. These spores can then re-circulate through the air conditioning system. Because of the moisture and temperature activity inside the evaporator and the lack of light, many of these contaminants and particles tend to accumulate inside the evaporator unit, creating layers of what appears to be "mud". When the air conditioning is turned on spores in the system can be blown out into the cabin which can actually create a health risk in certain individuals. At best, this situation creates an annoying bad-smelling odor every time the A/C and/or the heater are turned on.

Methods for removing or treating these mold, bacteria and odors inside the evaporator and ventilation system have been developed. One method is to spray a foaming aerosol solution through the evaporator drain hole. The foam then expands into foam inside the evaporator. However, the rapid expansion from an aerosol to a foam state prevents the foam from effectively reaching the upper recesses of the evaporator. In addition, the method is complicated by the need to either remove the evaporator or raise the vehicle on a lift in order to reach the drain hole, or drill a hole in the evaporator case to allow a straw type aerosol injector access. These are all labor intensive operations requiring a person to position the vehicle appropriately, position and hold the aerosol can while depressing the valve releasing its contents.

Another method involves spraying a non-foaming aerosol solution into the exterior-located air intake, while the blower motor is running. However, because the aerosol droplets of the spray are heavier than air, and significantly larger at about 40-100 microns in size. They do not travel effectively and far enough to reach the inside of the evaporator or the entire ventilation system. Neither of these solutions is designed to treat interior cabin surfaces for microorganisms and contaminants and both are labor-intensive in that the operator must continuously depress the valve on the aerosol can in order to release its contents. Airsept, Inc. provides one such product. Alternatively, electronics can be used to keep the evaporator dry. See e.g., U.S. Pat. Nos. 5,899,082 and 6,840,051.

Accordingly, is desirable to provide a corrosion resistance coating for an automotive heat exchanger component comprising an odor remediation coating, and a process for making such a heat exchanger component that is at least as reliable for making heat exchanger component surfaces requiring a relatively high level of corrosion resistance as that provided by conventional chromate and non-chromate chemical conversion coating methods.

SUMMARY

This section provides a general summary of the disclosure, and is not a comprehensive disclosure of its full scope or all of its features.

The applicants have discovered that automotive heat exchanger components (automotive heat exchanger components include: a heat exchanger, an evaporator, a heater core, a condenser, a radiator or combinations thereof) comprising a surface containing aluminum or aluminum alloy can be readily coated with a metal oxide ceramic coating and an odor neutralizing agent to form protective coatings that are corrosion resistant and possess odor remediation properties. The heat exchanger component can be anodized with an aqueous anodizing solution containing oxides, complex fluorides and/or complex oxyfluorides of metals including titanium, zirconium, vanadium, hafnium, tin, germanium, niobium and boron. The anodizing solution does not contain zinc and the process is substantially devoid, more preferably free of chromium, permanganate, borate, sulfate, free fluoride and free chloride. The anodizing solution contains one or more water soluble and/or water dispersible anionic species, including a metal, a metalloid and/or a non-metal element. The metal oxide ceramic coating disposed on the aluminum containing surface of the heat exchanger is also coated with an odor neutralizing agent that binds to the surface of the ceramic coating and pores contained thereon.

In one aspect of the present technology, the automobile heat exchanger component includes:

(A) a heat exchanger component having an aluminum surface;

(B) a metal oxide ceramic coating disposed on at least a portion of the aluminum surface; and (C) an odor neutralization agent coated on the ceramic coating thereby forming an odor neutralizing ceramic coating on the heat exchanger component.

In a further aspect of the present technology, an automotive metal oxide ceramic coated heat exchanger component is provided. The heat exchanger component comprises: a heat exchanger component having an aluminum surface; a ceramic coating disposed at least partially on the aluminum surface, the metal oxide ceramic coating having a component contact surface and an exterior surface. The ceramic coating is applied to the aluminum surface using plasma electrochemical deposition. The ceramic coating exterior surface has a plurality of pores as a result of the electrochemical deposition. The ceramic coating further includes an odor neutralizing agent disposed on the ceramic coating exterior surface and at least partially in the plurality of pores.

In some embodiments, the heat exchanger component is a component found in an automobile, such automobiles include: passenger cars, pickup trucks, minivans, sport-utility vehicles (SUVs), buses, delivery trucks, heavy duty trucks, semi-trucks, off-highway construction vehicles, e.g. escavators, bulldozers graders, scrapers and the like, passenger vans, two or three-wheeled motorcycles designed for on-road use, all-terrain vehicles (atvs), golf cars and other recreational vehicles. In some embodiments, the heat exchanger component can be made predominantly of aluminum or an aluminum alloy and is coated with a ceramic coating essentially made from titanium oxide, and wherein the titanium oxide coating is further coated with an odor neutralizing agent. Alternatively, the heat exchanger component is made from a composite material comprised of one or more of iron, steel, titanium, nickel, cobalt, niobium, vanadium, aluminum, tantalum, copper, magnesium, manganese, chromium, hafnium, tin and alloys thereof, carbon and ceramic sintered materials and wherein the heat exchanger component has at least one surface comprised essentially of aluminum or an aluminum alloy.

In a further aspect of the present technology, a method for forming a ceramic coated heat exchanger comprises: providing an anodizing solution comprising an aqueous water soluble complex of fluoride and/or oxyfluoride of a metal ion selected from one or more of titanium, zirconium, hafnium, tin, aluminum, germanium and boron, placing a cathode in the anodizing solution and a heat exchanger component having an aluminum surface as an anode in the anodizing solution, applying a pulsed current across the cathode and the anode through the anodizing solution for a period of time effective to coat the aluminum surface at least partially with a metal oxide on the surface of the aluminum surface to form a ceramic coating, removing the heat exchanger component from the anodizing solution and applying an odor neutralizing agent to the surface of the ceramic coating to form an anti-odor coating on the ceramic coating.

The current used to pass through the cathode, anode and anodizing solution can include pulsed direct current, non-pulsed direct current and/or alternating current. The pulsed current can have an average voltage of not more than 500 volts, or not more than 450 volts, or more preferably, not more than 400 volts. Desirably, at least to reduce coating time and cost, the average voltage of the pulsed direct current is at least 75 volts, desirably 100 volts. The peak voltage, when pulsed current is being used, is preferably not more than 600, preferably 500, most preferably 400 volts. Higher peak voltage may be used but generates more heat and tends to be less economical than the above-described voltages. In some embodiments, the peak voltage for pulsed current is not more than 600, 575, 550, 525, 500 volts and independently not less than 200, 250, 300, 310, 320, 330, 340, 350, 360, 370, 380, 390, 400 volts. Lower peak voltages may be used but the coating quality can be negatively affected as the peak voltage is reduced. The foregoing voltages for pulsed direct current are applicable in the presence or absence of any phosphorus containing components. When alternating current is being used, the voltage may range from 200 to 600 volts. In some embodiments the alternating current voltage can be less than 600, 575, 550, 525, 500 volts and independently not less than 300, 310, 320, 330, 340, 350, 360, 370, 380, 390, 400 volts. In the presence of phosphorus containing components, non-pulsed direct current, also known as straight direct current, may be used at voltages from 200 to 600 volts. The non-pulsed direct current desirably has a voltage of, in increasing order of preference 600, 575, 550, 525, 500 volts and independently not less than 300, 310, 320, 330, 340, 350, 360, 370, 380, 390, 400 volts.

In another aspect, the present technology provides for a method for forming a heat exchanger having a ceramic odor neutralizing coating, the method comprising: providing an anodizing solution comprised of water, a phosphorus containing acid and/or salt, and one or more additional components selected from the group consisting of: water-soluble complex fluorides, water-soluble complex oxyfluorides, water-dispersible complex fluorides, and water-dispersible complex oxyfluorides of elements selected from the group consisting of Ti and Zr, placing a cathode in the anodizing solution and a heat exchanger component having a surface of an aluminum or aluminum alloy as an anode in the anodizing solution, passing a pulsed current across the cathode and the anode through the anodizing solution for a period of time effective to form a ceramic Ti or Zr metal oxide coating (e.g. $TiO_2$) on at least one surface of the article, and coating the protective Ti or Zr metal oxide coating with an odor neutralization agent.

It is an object of the present technology to provide a method of forming a heat exchanger component having a surface comprised of aluminum with a ceramic odor neutralizing coating thereon, the method comprising: providing an anodizing solution, the anodizing solution having been prepared by combining one or more water-soluble complex fluorides of titanium and/or zirconium or salts thereof, a phosphorus containing oxy acid and/or salt and optionally, an oxide, hydroxide, carbonate or alkoxide of titanium and/or zirconium; providing a cathode in contact with the anodizing solution; placing a heat exchanger component comprised of aluminum as an anode in the anodizing solution; and passing a direct current or an alternating current between the anode and the cathode for a time effective to form the ceramic odor neutralizing coating on a surface of the heat exchanger component; removing the heat exchanger component having a ceramic odor neutralizing coating from the anodizing solution and drying the article; and applying one or more layers of an odor remediating coating material to the heat exchanger component having a ceramic odor neutralizing coating, at least one of the layers comprising an odor neutralizing agent, to form a odor remediating coating.

It is a further object of the present technology to provide a method of coating a heat exchanger component with a metal oxide ceramic coating wherein the article surface comprises predominantly aluminum. The heat exchanger component can be manufactured from any material including metals, e.g. iron, steel, titanium, nickel, cobalt, niobium, aluminum, tantalum, copper, magnesium, manganese, vanadium, chromium, hafnium, tin and alloys thereof and ceramic materials used in the manufacture of heat exchanger components, provided that the heat exchanger has at least an aluminum surface to be coated with the ceramic coating. It is a further object of the present technology to provide a method wherein the ceramic coating comprises predominantly oxides (e.g. O, $O_2$) of one or more of Ti, Zr, Hf, Sn, Ge and/or B. It is a further object to provide a method wherein the heat exchanger component comprises a surface containing predominantly aluminum and the ceramic coating is predominantly titanium oxide ($TiO_2$).

It is a further object to provide a method wherein the current is pulsed direct current having an average voltage of not more than 200 volts. In some embodiments, the protective coating is predominantly comprised of titanium oxide. The protective coating is preferably formed at a rate of at least 1 micron thickness per minute; the current is preferably pulsed direct current or alternating current. In some embodiments, the anodizing solution comprises water, a phosphorus containing acid and water-soluble and/or water-dispersible complex fluorides of Ti and/or Zr. Preferably the pH of the anodizing solution is 1-6.

The ceramic coating is further coated with an odor neutralizing agent. The odor neutralizing agent can include one or more of an odor capture agent, a fragrance agent and an antimicrobial agent, thereby forming an odor neutralizing ceramic coating.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 depicts a transmission electron photograph of a heat exchanger coated with a titanium metal oxide on the surface of the heat exchanger component in accordance with the present technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present technology, and are not intended to limit the disclosure of the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting ingredients, components or process steps, Applicants specifically envision embodiments consisting of, or consisting essentially of, such ingredients, components or processes excluding additional ingredients, components or processes (for consisting of) and excluding additional ingredients, components or processes affecting the novel properties of the embodiment (for consisting essentially of), even though such additional ingredients, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

Automotive Heat Exchanger Components

The present technology provides methods for making automotive heat exchanger components having an aluminum surface coated with a metal oxide ceramic. The aluminum surface is coated with a metal oxide ceramic coating, preferably titanium or zirconium oxide using electrochemical deposition of titanium and zirconium metal ions in an aqueous anodizing solution. The titanium or zirconium metal oxide coating formed on the aluminum surface of the heat exchanger component is then coated with an odor neutralizing agent, thereby an odor neutralizing ceramic coating. As used herein the titanium oxide or zirconium oxide coatings prepared by the methods of the present technology are referred to herein as metal oxide ceramic coatings and ceramic coatings which are used interchangeably herein.

There is no specific limitation on the aluminum or aluminum heat exchanger component to be subjected to anodization in accordance with the present technology. It is desirable that at least a portion of the heat exchanger component is fabricated from a metal that contains not less than 50% by weight, more preferably not less than 70% by weight aluminum. Preferably, the article is fabricated from a metal that contains not less than, in increasing order of preference, 30, 40, 50, 60, 70, 80, 90, 100% by weight aluminum. Preferably, the heat exchanger component has a surface that contains at least 50% by weight aluminum.

The automotive heat exchanger components of the present technology includes heat exchangers, evaporators, condensers, radiators and charge coolers that are used in road-use automotive vehicles, including, but are not limited to, passenger cars, pickup trucks, minivans, sport-utility vehicles (SUVs), buses, light, medium and heavy duty-trucks, passenger vans, two or three-wheeled motorcycles designed for on-road use, all-terrain vehicles (atvs) and golf cars.

Method for Coating Heat Exchanger Components with an Odor Neutralizing Ceramic Coating In some embodiments, a generalized process for making an odor neutralizing ceramic coated heat exchanger component includes:
1. Surface preparation by degreasing with hot water or optionally an aqueous solution containing an acidic, alkaline, or solvent-based system;
2. Rinsing with de-ionized water;
3. Surface treating the heat exchanger component with plasma electrochemical deposition in an anodizing solution according to the present technology, wherein the treatment temperature is ambient temperature to about 80° C. and the plasma electrochemical deposition treatment time ranges is generally at least about 30 seconds and not more than about 30 minutes, desirably from about 60 seconds to about 20 minutes, and in some embodiments, from about 1 to about 5 minutes, preferably from about 2 to about 4 minutes;
4. Air drying the ceramic coated heat exchanger component;
5. Coating the ceramic coated heat exchanger component with an odor neutralization agent
6. Optionally, rinsing the coated heat exchanger component with de-ionized water; and
7. Drying the odor neutralizing ceramic coated heat exchanger component at ambient temperatures.

Optionally, an odor neutralization agent can be added to the electrolytic bath, provided that the agent is stable to the conditions of the electrolytic deposition process and the agent does not unduly interfere with same. In this process, step 5, above, can be included or eliminated in processes according to the invention.

Surface Preparation

Before being subjected to anodic treatment in accordance with the present technology, the aluminum containing surface of the heat exchanger component is preferably subjected to a cleaning and/or degreasing step using hot water. In some embodiments, the heat exchanger component can also be chemically degreased by exposure to an alkaline cleaner such as, for example, a diluted solution of PARCO Cleaner 305 (a product of the Henkel Surface Technologies division of Henkel Corporation, Madison Heights, Mich.). After cleaning, the article preferably is rinsed with water. Such pre-anodization treatments are well known in the art.

Electrochemical Deposition of a Metal Oxide Ceramic Coating

The heat exchanger component is coated with a metal oxide using plasma electrochemical deposition. Methods for forming a metal oxide on a metal article containing aluminum alloy surface having utility in the present technology are described in U.S. Pat. No. 7,452,454, Ser. No. 10/972,951, Issued Nov. 18, 2008, and U.S. Patent Application Publication Nos. 2005/0115840, Ser. No. 10/972,592, published Jun. 2, 2005, 2005/0061680, Ser. No. 10/972,594, published Mar. 24, 2005 and 2006/0013986, Ser. No. 11/156,425, published Jan. 19, 2006. All four references are hereby incorporated in their entirety herein.

In some embodiments, the anodization of a heat exchanger component includes an anodizing solution maintained at a temperature between 0° C. and 90° C. It is desirable that the temperature of the anodizing solution be kept at least 5, 10, 15, 20, 25, 30, 40, 50° C. and not more than 90, 88, 86, 84, 82, 80, 75, 70, 65° C. The anodization process includes the steps of immersing at least a portion of the heat exchanger component in the anodizing solution, which is preferably contained within a bath, tank or other such container. The heat exchanger component functions as the anode. A second metal article that is cathodic relative to the heat exchanger component is also placed in the anodizing solution. Alternatively, the anodizing solution is placed in a container which is itself cathodic relative to the heat exchanger component (anode). When using pulsed current, in one embodiment, an average voltage potential not in excess of 250 volts, 200 volts, 175 volts, 150 volts, 125 volts is then applied across the electrodes until a coating of the desired thickness is formed on an aluminum surface of the heat exchanger component in contact with the anodizing solution. When certain anodizing solution compositions are used, good results may be obtained even at average voltages not in excess of 100 volts. It has been observed that the formation of a metal oxide ceramic coating is often associated with anodization conditions which are effective to cause a visible light-emitting discharge (sometimes referred to herein as a "plasma", although the use of this term is not meant to imply that a true plasma exists) to be generated (either on a continuous or intermittent or periodic basis) on the aluminum surface of the heat exchanger component, and hence the process plasma electrochemical deposition.

In some embodiments, direct current (DC) is used at 10-400 Amps/square foot and 150 to 600 volts. In another embodiment, the current is pulsed or pulsing current. Non-pulsed direct current is desirably used in the range of 200-600 volts; preferably the voltage is at least, about 200, about 250, about 300, about 350, or about 400 volts and at least not more about 700, or about 650, or about 600, or about 550 volts. Direct current can be used, although alternating current may also be utilized (under some conditions, however, the rate of coating formation may be lower using AC). The frequency of the wave may range from 10 to 10,000 Hertz; higher frequencies may be used. The "off" time between each consecutive voltage pulse preferably lasts between 10% as long as the voltage pulse and 1000% as long as the voltage pulse. During the "off" period, the voltage need not be dropped to zero (i.e., the voltage may be cycled between a relatively low baseline voltage and a relatively high ceiling voltage). The baseline voltage can be adjusted to a voltage that is from 0% to 99.9% of the peak applied ceiling voltage. Low baseline voltages (e.g., less than 30% of the peak ceiling voltage) tend to favor the generation of a periodic or intermittent visible light-emitting discharge, while higher baseline voltages (e.g., more than 60% of the peak ceiling voltage) tend to result in continuous plasma anodization (relative to the human eye frame refresh rate of 0.1-0.2 seconds). The current can be pulsed with either electronic or mechanical switches activated by a frequency generator. The average amperage per square foot is at least 10, 20, 30, 40, 50, 60, 70, 80, 90, 100, 105, 110, 115, and not more than at least 300, 275, 250, 225, 200, 180, 170, 160, 150, 140, 130, 125 amps. More complex waveforms can also be employed, for example, a DC signal having an AC component. Alternating current may also be used, with voltages desirably between 200 and 600 volts. The higher the concentration of the electrolyte in the anodizing solution, the lower the voltage can be while still depositing satisfactory metal oxide coatings.

A number of different types of anodizing solutions can be successfully used in the methods of the present technology, as will be described in more detail hereinafter. However, it is believed that a wide variety of water-soluble or water-dispersible anionic species containing metal, metalloid, and/or non-metal elements are suitable for use as components of the anodizing solution. Representative elements include, for example, phosphorus, titanium, zirconium, hafnium, tin, germanium, boron, vanadium, fluoride, zinc, niobium, molybdenum, manganese, tungsten, tantalum, silicon, scandium, cerium, yttrium, calcium, magnesium and the like (including combinations of such elements). In some embodiments, of the present technology, the components of the anodizing solution are titanium and/or zirconium.

Without wishing to be bound by theory, it is thought that the anodization of a heat exchanger component having an aluminum or aluminum alloy surface in the presence of complex fluoride or oxyfluoride species to be described subsequently in more detail leads to the formation of surface coating or films comprised of metal/metalloid oxide ceramics e.g. titanium or zirconium oxide (including partially hydrolyzed glasses containing O, OH and/or F ligands) or metal/non-metal compounds wherein the metal comprising the surface film includes metals from the complex fluoride or oxyfluoride species and some metals from the article. The plasma or sparking which often occurs during anodization in accordance with the present technology is believed to destabilize the anionic species, causing certain ligands or substituents on such species to be hydrolyzed or displaced by O and/or OH or metal-organic bonds to be replaced by metal-O or metal-OH bonds. Such hydrolysis and displacement reactions render the species less water-soluble or water-dispersible, thereby driving the formation of the surface coating of oxide that forms the second protective coating. A pH adjuster may be present in the anodizing solution; suitable pH adjusters include, by way of nonlimiting example, ammonia, amine or other base. The amount of pH adjuster is limited to the amount required to achieve a pH of 1-6.5, preferably 2-6, most preferably 3-5, and is dependent upon the type of electrolyte used in the anodizing bath. In a preferred embodiment, the amount of pH adjuster is less than 1% w/v.

In some embodiments of the present technology, the anodizing solution is essentially (more preferably, entirely) free of chromium, permanganate, borate, sulfate, free fluoride and/or free chloride.

The anodizing solution used preferably comprises water and at least one complex fluoride or oxyfluoride of an element selected from the group consisting of Ti, Zr, Hf, Sn, Al, Ge and B (preferably, Ti and/or Zr). The complex fluoride or oxyfluoride compounds should be water-soluble or water-dispersible and preferably comprises an anion comprising at least 1 fluorine atom and at least one atom of an element selected from the group consisting of Ti, Zr, Hf, Sn, Al, Ge or B. The complex fluorides and oxyfluorides (sometimes referred to by workers in the field as "fluorometallates") preferably are substances with molecules having the following general empirical formula (I): $H_pT_qF_rO_s$ (I) wherein: each of p, q, r, and s represents a non-negative integer; T represents a chemical atomic symbol selected from the group consisting of Ti, Zr, Hf, Sn, Al, Ge, and B; r is at least 1; q is at least 1; and, unless T represents B, (r+s) is at least 6. One or more of the H atoms may be replaced by suitable cations such as ammonium, metal, alkaline earth metal or alkali metal cations (e.g., the complex fluoride may be in the form of a salt, provided such salt is water-soluble or water-dispersible).

Illustrative examples of suitable complex fluorides include, but are not limited to, $H_2TiF_6$, $H_2ZrF_6$, $H_2HfF_6$, $H_2GeF_6$, $H_2SnF_6$, $H_3AlF_6$, and $HBF_4$ and salts (fully as well as partially neutralized) and mixtures thereof. Examples of suitable complex fluoride salts include $SrZrF_6$, $MgZrF_6$, $Na_2ZrF_6$ and $Li_2ZrF_6$, $SrTiF_6$, $MgTiF_6$, $Na_2TiF_6$ and $Li_2TiF_6$. The total concentration of complex fluoride and complex oxyfluoride agents in the anodizing solution preferably is at least 0.005 M. Generally, there is no preferred upper concentration limit, except of course for any solubility constraints. It is desirable that the total concentration of complex fluoride and complex oxyfluoride in the anodizing solution be at least 0.005, 0.010, 0.020, 0.030, 0.040, 0.050, 0.060, 0.070, 0.080, 0.090, 0.10, 0.20, 0.30, 0.40, 0.50, 0.60 M, and be not more than 2.0, 1.5, 1.0, 0.80 M.

To improve the solubility of the complex fluoride or oxyfluoride, especially at higher pH, it may be desirable to include an inorganic acid (or salt thereof) that contains fluorine but does not contain any of the elements Ti, Zr, Hf, Sn, Al, Ge or B in the electrolyte composition. Hydrofluoric acid or a salt of hydrofluoric acid such as ammonium bifluoride is preferably used as the inorganic acid. The inorganic acid is believed to prevent or hinder premature polymerization or condensation of the complex fluoride or oxyfluoride, which otherwise (particularly in the case of complex fluorides having an atomic ratio of fluorine to T of 6) may be susceptible to slow spontaneous decomposition to form a water-insoluble oxide. Certain commercial sources of hexafluorotitanic acid and hexafluorozirconic acid are supplied with an inorganic acid or salt thereof, but it may be desirable in certain embodiments of the present technology to add still more inorganic acid or inorganic salt.

A chelating agent, especially a chelating agent containing two or more carboxylic acid groups per molecule such as nitrilotriacetic acid, ethylene diamine tetraacetic acid, N-hydroxyethyl-ethylenediamine triacetic acid, or diethylenetriamine pentaacetic acid or salts thereof, can also be included in the anodizing solution. Other Group IV compounds can be used, for example, Ti and/or Zr oxalates and/or acetates, as well as other stabilizing ligands, such as acetylacetonate, glucoheptanate and other chelating agents known in the art that do not interfere with the anodic deposition of the anodizing solution and normal bath lifespan, and have a suitable stability in the bath under deposition conditions. In particular, it is necessary to avoid organic materials that either decompose or undesirably polymerize in the energized anodizing solution.

Rapid coating formation is generally observed at average voltages of 100-400, preferably 150-350 volts, using pulsed DC. It is desirable that the average voltage be of sufficient magnitude to generate coatings of the present technology at a rate of at least 1 micron thickness per minute, preferably at least 3-8 microns in 3 minutes. In some embodiments, it is desirable that the average voltage be less than 300, 200, 150, 140, 130, 125, 120, 115, 110, 100, 90 volts. Desirably, the minimum average voltage for pulsed direct current is at least 50, 60, 70, 80 volts. The time required to deposit a coating of a selected thickness is inversely proportional to the concentration of the anodizing bath and the amount of current Amps/square foot used. In some illustrative examples, heat exchanger components having an aluminum surface can be coated with an 8 micron thick metal (Ti or Zr) oxide layer in as little as 10-15 seconds at concentrations of $H_2TiF_6$ ranging from 5-30 g/l and $H_3PO_4$ ranging from 1-10 g/L by increasing the Amps/square foot to 300-2000 amps/square foot. The determination of correct concentrations and current amounts for optimum part coating in a given period of time can be made by one of skill in the art based on the teachings herein with routine experimentation.

Metal oxide ceramic coatings of the present technology are typically fine-grained and desirably are at least 1 micron thick, ranging from 1-20, of from 1-10 microns. The morphology of the metal oxide ceramic coatings may be amorphous or contain crystalline domains. The presence or absence of crystalline structure does not affect performance of the ceramic coating. In some embodiments the ceramic coating can have a thicknesses ranging from about 1 micron to about 20 microns, or from about 1 micron to about 15 microns, or from about 1 micron to about 10 microns, or from about 1 micron to about 5 microns, or from about 2 microns to about 20 microns, or from about 5 microns to about 20 microns, or from about 7 microns to about 20 microns, or from about 10 microns to about 20 microns. Thinner or thicker coatings may be applied, although thinner coatings less than 1 micron may not provide the desired coverage of the article. Without being bound by any specific theory, it is believed that, particularly for insulating oxide films, as the coating thickness increases, the film deposition rate is eventually reduced to a rate that approaches zero asymptotically. Add-on mass of coatings of the present technology ranges from approximately 5-200 $g/m^2$ or more and is a function of the coating thickness and the composition of the coating. It is desirable that the add-on mass of coatings be at least, 5, 10, 11, 12, 14, 16, 18, 20, 25, 30, 35, 40, 45, 50 $g/m^2$. Despite the insulating nature of the ceramic coating vis a vis further deposition, and contrary to expectations, the heat insulating character of the ceramic oxide coating does not substantially reduce heat exchange of the coated heat exchanger as compared to a similar uncoated heat exchanger. Without being bound by a single theory, Applicants believe that the increased surface area provided by the ceramic oxide coating compensates for any insulating properties of the ceramic material.

In a some embodiments of the present technology, the anodizing solution used comprises water, a water-soluble and/or water-dispersible phosphorus oxy acid or salt, for instance an acid or salt containing phosphate anion; and at least one of $H_2TiF_6$ and $H_2ZrF_6$. Preferably, the pH of the anodizing solution is neutral to acid (more preferably, pH ranging 6.5 to 2).

It was surprisingly found that the combination of a phosphorus containing acid and/or salt and the complex fluoride in the anodizing solution produced a different type of anodically deposited metal oxide coating. The metal oxide coatings deposited comprised predominantly oxides of anions present in the anodizing solution prior to any dissolution of the anode. That is, this process results in coatings that result predominantly from deposition of substances that are not drawn from the body of the anode, resulting in less change to the substrate of the heat exchanger component being anodized. Phosphorus is also present in metal oxide coatings deposited from phosphorus-containing electrolytes, usually in the form of metal phosphates, for example some titanium phosphate is found in titania coatings according to the invention. In some embodiments, it is desirable that the anodizing solution comprise the at least one complex fluoride, e.g. $H_2TiF_6$ and/or $H_2ZrF_6$ in an amount of at least, 0.2, 0.4, 0.6, 0.8. 1.0, 1.2, 1.3, 1.4, 1.5, 2.0, 2.5, 3.0, 3.5 wt. % and not more than, 10, 9.5, 9.0, 8.5, 8.0, 7.5, 7.0, 6.5, 6.0, 5.5, 5.0, 4.5. 4.0 wt. %. The at least one complex fluoride can be supplied from any suitable source for example, various aqueous solutions known in the art. For $H_2TiF_6$ commercially available solutions typically range in concentration from 50-60 wt %; while for $H_2ZrF_6$ such solutions range in concentration between 20-50 wt %.

The phosphorus oxysalt can be supplied from any suitable source, for example, ortho-phosphoric acid, pyro-phosphoric acid, tri-phosphoric acid, meta-phosphoric acid, polyphosphoric acid and other combined forms of phosphoric acid, as well as phosphorous acids and hypo-phosphorous acids, and can be present in the anodizing solution in partially or fully neutralized form (e.g., as a salt, wherein the counter ion(s) are alkali metal cations, ammonium or other such species that render the phosphorus oxysalt watersoluble). Organophosphates such as phosphonates and the like may also be used (for example, various phosphonates are available from Rhodia Inc. and Solutia Inc.) provided that the organic component does not interfere with the anodic deposition.

Particularly preferred is the use of a phosphorus oxysalt in acid form. The phosphorus concentration in the anodizing solution is at least 0.01 M. It is preferred that the concentration of phosphorus in the anodizing solution be at least 0.01M, 0.015, 0.02, 0.03, 0.04, 0.05, 0.07, 0.09, 0.10, 0.12, 0.14, 0.16. In embodiments where the pH of the anodizing solution is acidic (pH<7), the phosphorus concentration can be 0.2 M, 0.3 M or more and preferably is not more than 1.0, 0.9, 0.8, 0.7, 0.6 M. In embodiments where the pH is neutral to basic, the concentration of phosphorus in the anodizing solution is not more than 0.40, 0.30, 0.25 or 0.20 M.

In some embodiments, an illustrative example of an anodizing solution for use in forming a ceramic coating according to this embodiment on an aluminum or aluminum alloy containing surface of a heat exchanger component can be prepared using the following components: $H_2TiF_6$ (0.05 to 10 wt. %), $H_3PO_4$ (0.1 to 0.6 wt. %) Water Balance to 100%. The pH is adjusted to the range of 2 to 6 using ammonia, amine or other base.

With the above described anodizing solutions, the generation of a sustained "plasma" (visible light emitting discharge) during anodization is generally attained using pulsed DC having an average voltage of no more than 50-600 volts.

In some embodiments, the average pulse voltage can range from 100-500 volts. Non-pulsed direct current, so called "straight DC" or alternating current can also be used with average voltages ranging from 300-600 volts.

Without wishing to be bound by any particular theory, it is believed that the anodization of aluminum containing metals in the presence of such species using low voltage pulsed current leads to the formation of surface coatings comprised of metal/metalloid oxide ceramics (including partially hydrolyzed glasses containing O, OH and/or F ligands) or light metal/non-metal compounds. The low voltage plasma or sparking which occurs during anodization is believed to destabilize the anionic species, causing certain ligands or substituents on such species to be hydrolyzed or displaced by O and/or OH or metal-organic bonds to be replaced by metal-O or metal-OH bonds otherwise known as ligand-exchange. Such hydrolysis and ligand-exchange reactions render the species less water-soluble or waterdispersible, thereby driving the formation of the metal oxide ceramic coating.

In certain embodiments of the invention, the anodizing solution is essentially (more preferably, entirely) free of ammonia, chromium, zinc permanganate, borate, sulfate, free fluoride and/or free chloride.

The anodized coatings produced in accordance with the invention typically range in color from blue-grey and light grey to charcoal grey depending upon the coating thickness and relative amounts of Ti and/or Zr in the coatings. The metal oxide ceramic coatings exhibit high hiding power at coating thicknesses of 1-20 microns, and excellent corrosion resistance using various known tests in the field of automotive heat exchanger manufacture. Table 1 shows a comparative sample using non-chromate conversion process ratings versus heat exchanger components that have been plasma electrochemically coated according to a method of the present technology resulting in an 3-micron thick coating layer of a ceramic predominantly comprising titanium oxide. The titanium coated substrate shown in FIG. 1 was light grey in color, but provided good hiding power. Readily observable in FIG. 1 are a plurality of pores distributed throughout the metal oxide ceramic coating. In some embodiments, a plurality of pores can be formed along the surface of the metal oxide ceramic coating.

Odor Neutralization Coatings

The present technology provides heat exchanger components that provide ceramic coatings having properties relating to both corrosion resistance and odor remediation. The present technology offers several advantages compared to prior art chromate and non-chromate chemical conversion coating processes, for example, reduction in process waste streams, including reduction in efferent acids, organic resins, solvents and metal ions. The plasma electrochemical deposition coating processes of the present technology obviates the need to coat the heat exchanger components with caustic acids, VOCs and organic and hydrophilic resins as used in prior art surface treatment processes which offers substantial reduction in process waste, environmental damage and resources. The heat exchanger component of the present technology comprises an odor remediation coating which includes one or more odor neutralization agents coated on the surface of the metal oxide ceramic coating. The odor neutralization agent can include an odor capture agent, a fragrance agent and an antimicrobial agent. The concentration of each odor neutralization agents within the odor remediation coating can range from 0.0001% to about 40% wt %. In some embodiments, the odor neutralization agent can be coated on a metal oxide coating formed in accordance with the present methods in an amount ranging from about 0.1 to about 1, from about 5 to about 10, from about 10 to about 50, from about 100 to about 300 and from about 300 to about 3,000 mg/m² or more. In some embodiments, the odor remediation coating can also include one or more carriers, excipients, coating enhancers and the like known in the art of odor remediation coating technology. The odor remediation coating can contain one or more carriers that are compatible with the odor neutralization agent, does not overly mask the scent or activity of the odor neutralization agent and assists in retaining the odor neutralization agent to the surface of the metal oxide ceramic coating.

In some embodiments, the odor remediation coating can include one or more layers comprising an odor neutralization agent which may be the same or may be different. The odor neutralization agent can be formulated and applied with either a hydrophilic or hydrophobic carrier depending on the chemical compatibility of the odor neutralization agent. If the odor neutralization agent is lipophilic, then an organic solvent or other hydrophobic carrier can be used to solubulize the lipophilic odor neutralization agents prior to application.

Odor Capture Agents

The odor neutralization agent can include one or more odor capture agents formulated to be coated over a metal oxide ceramic coating deposited onto a heat exchanger using plasma electrochemical deposition. The term "odor capture agent" refers to any molecule capable of bonding to an odor causing compound including amines, sulfides, thiols and volatile organic compounds.

One such class of odor capture agents which finds utility in the present technology include cyclodextrins. Cyclodextrins have a toroidal structure, the interior of which is hydrophobic. The exterior of this toroid structure is hydrophilic thereby rendering them water-soluble. It has been found that hydrophobic odor-causing compounds enter the hydrophobic interior of a cyclodextrin toroid and form a stable complex with the cyclodextrin structure due to the interplay of Van der Waals forces, the effects of hydrogen bonding and the common hydrophobicity of the cyclodextrin interior and odor-causing molecule. By forming stable complexes with odor-causing molecules, cyclodextrins trap the odor causing molecules thereby reducing the odor caused thereby.

As used herein, the term "cyclodextrin" includes any of the known cyclodextrins, for example, unsubstituted cyclodextrins containing from six to twelve glucose units, especially, alpha, beta, and gamma-cyclodextrins, and/or their derivatives, and/or mixtures thereof. The alpha-cyclodextrin consists of six glucose units, the beta-cyclodextrin consists of seven glucose units, and the gamma-cyclodextrin consists of eight glucose units arranged in donut-shaped rings. The specific coupling and conformation of the glucose units give the cyclodextrins a rigid, conical molecular structures with hollow interiors of specific volumes. The "lining" of each internal cavity is formed by hydrogen atoms and glycosidic bridging oxygen atoms; therefore, this surface is fairly hydrophobic. The unique shape and physical-chemical properties of the cavity enable the cyclodextrin molecules to absorb (form inclusion complexes with) organic molecules or parts of organic molecules which can fit into the cavity. Many odorous molecules can fit into the cavity including many malodorous molecules and perfume molecules. Therefore, cyclodextrins, and especially mixtures of cyclodextrins with different size cavities, can be used to control odors caused by a broad spectrum of organic odoriferous materials, which may, or may not, contain reactive functional groups. The complexation between cyclodextrin and odorous molecules occurs rapidly in the presence of water. However, the extent of the complex formation also depends on the polarity of the absorbed molecules. In an aqueous solution, strongly hydrophilic molecules (those which are highly water-soluble) are only partially absorbed, if at all. Therefore, cyclodextrin does not complex effectively with some very low molecular weight organic amines and acids when they are present at low levels on wet fabrics. As the water is being removed however, e.g., the fabric is being dried off, some low molecular weight organic amines and acids have more affinity and will complex with the cyclodextrins more readily. These cavities can be filled with all or a portion of an organic molecule with suitable size to form an "inclusion complex." Alpha-, beta-, and gamma-cyclodextrins can be obtained from, among others, American Maize-Products Company (Amaizo), Hammond, Ind.

Cyclodextrin derivatives are disclosed in U.S. Pat. Nos. 3,426,011, Parmerter et al., issued Feb. 4, 1969; 3,453,257, 3,453,258, 3,453,259, and 3,453,260, all in the names of Parmerter et al., and all also issued Jul. 1, 1969; 3,459,731, Gramera et al., issued Aug. 5, 1969; 3,553,191, Parmerter et al., issued Jan. 5, 1971; 3,565,887, Parmerter et al., issued Feb. 23, 1971; 4,535,152, Szejtli et al., issued Aug. 13, 1985; 4,616,008, Hirai et al., issued Oct. 7, 1986; 4,638,058, Brandt et al., issued Jan. 20, 1987; 4,746,734, Tsuchiyama et al., issued May 24, 1988; and 4,678,598, Ogino et al., issued Jul. 7, 1987, all of said patents being incorporated herein by reference. Examples of cyclodextrin derivatives suitable for use as odor capture agents can include methyl-β-cyclodextrin, hydroxyethyl-β-cyclodextrin, and hydroxypropyl-β-cyclodextrin of different degrees of substitution (D.S.), available from Amaizo; Wacker Chemicals (USA), Inc.; and Aldrich Chemical Company. Water-soluble derivatives are also highly desirable.

The individual cyclodextrins can also be linked together, e.g., using multifunctional agents to form oligomers, polymers, etc. Examples of such materials are available commercially from Amaizo and from Aldrich Chemical Company (beta-cyclodextrin/epichlorohydrin copolymers).

The odor capture agent can include a specific formulation of cyclodextrin for example Febreze™. Febreze™ also relates to concentrated compositions, wherein the level of cyclodextrin is from about 3% to about 20%, more preferably from about 5% to about 10%, by weight of the composition which are diluted to form compositions with the usage concentrations of cyclodextrin of, e.g., from about 0.1% to about 5%, by weight of the diluted composition, as given hereinabove, which are to the "usage conditions".

The cavities within the cyclodextrin in the odor capture agent solution of the present technology should remain essentially unfilled (the cyclodextrin remains uncomplexed) while in solution, in order to allow the cyclodextrin to absorb various odor molecules when the odor capture agent is applied to a porous surface of the ceramic coating. Non-derivatised (normal) beta-cyclodextrin can be present at a level up to its solubility limit of about 1.85%, (about 1.85 g in 100 grams of water) at room temperature.

In some embodiments, odor capture agents comprising Febreze™ have cyclodextrins that are highly water-soluble such as, alpha cyclodextrin and/or derivatives thereof, gamma cyclodextrin and/or derivatives thereof, derivatised beta cyclodextrin, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a—$CH_2$—CH(OH)—$CH_3$ or a—$CH_2CH_4$—OH group; branched cyclodextrins such as maltose-bonded cyclodextrins; cationic cyclodextrins such as those containing 2-hydroxy-3-(dimethylamino)propyl ether, wherein R is $CH_2$—CH(OH)—$CH_2$—$N(CH_3)_2$ which is cationic at low pH; quaternary ammonium, e.g., 2-hydroxy-3-(trimethylammonio)propyl ether chloride groups, wherein R is $CH_2$—CH(OH)—$CH_2$—$N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins Highly water-soluble cyclodextrins are those having water solubility of at least about 10 g in 100 mL of water at room temperature, preferably at least about 20 g in 100 mL of water, more preferably at least about 25 g in 100 mL of water at room temperature. The availability of solubilized, uncomplexed cyclodextrins is preferred for effective and efficient odor control performance.

Non-limiting examples of water-soluble cyclodextrin derivatives suitable for use herein include hydroxypropyl alpha-cyclodextrin, methylated alpha-cyclodextrin, methylated β-cyclodextrin, hydroxyethyl β-cyclodextrin, and hydroxypropyl β-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl-β-cyclodextrin, commonly known as DIMEB, in which each glucose unit has about 2 methyl groups with a degree of substitution of about 14. A preferred, more commercially available, methylated β-cyclodextrin is a randomly methylated β-cyclodextrin, commonly known as RAMEB, having different degrees of substitution, normally of about 12.6. RAMEB is more preferred than DIMEB, since DIMEB affects the surface activity of the preferred surfactants more than RAMEB. The preferred cyclodextrins are available, e.g., from Cerestar U.S.A., Inc. and Wacker Chemicals (U.S.A.), Inc.

In some embodiments, the odor capture agent can include a mixture of cyclodextrins. Such mixtures absorb odors more broadly by complexing with a wider range of odoriferous molecules having a wider range of molecular sizes. Preferably at least a portion of the cyclodextrins is alpha cyclodextrin and its derivatives thereof; gamma cyclodextrin and its derivatives thereof, and/or derivatised beta cyclodextrin, more preferably a mixture of alpha cyclodextrin, or an alpha cyclodextrin derivative, and derivatised beta cyclodextrin, even more preferably a mixture of derivatised alpha cyclodextrin and derivatised beta cyclodextrin, most preferably a mixture of hydroxypropyl alpha-cyclodextrin and hydroxypropyl beta cyclodextrin, and/or a mixture of methylated alpha cyclodextrin and methylated beta cyclodextrin.

Other odor capture agents finding utility as odor capture agents can include: esters of alpha, beta unsaturated monocarboxylic acids, cyclohexyl alcohols and ester derivatives, fumaric acid esters, cyclohexyl alkyl ketones, acetic and propionic acids, 4-cyclohexyl-4-methyl-2-pentanone, Ordenone™ by Belle-Aire Fragrance, Odor Trap™ by U.S. Flavor and Fragrance, Flexisorb OD-100 by Innovative Chemical Technology Inc., Meelium™ by Prentiss Inc., Tego SorbTMConc. 50 by Goldschmidt Chemical Corp., undecylenic acid and derivatives thereof, zeolites and the like.

Odor capture agents can also include a simple metal carbonate or metal hydrogen carbonates can also be absorbed by the coating by water solution application and drying. Activated carbon (aqueous or non-aqueous) dispersions could also be dried on the surface as an odor capture agent (and be applied to the inside the pores of the coating if small enough carbon dispersion particles are selected).

Fragrance Agents

The odor neutralization agent can include one or more fragrance or perfume agents known in the art. Selection of any fragrance agent, or amount of fragrance in the coating composition, is based on organoleptic, functional and aesthetic considerations, readily determinable to those of ordinary skill in the art with minimal experimentation. Fragrance agents useful in the present technology can include the highly volatile, and the moderately volatile fragrance agents, more preferably the highly volatile, low boiling fragrance agents.

The highly volatile, low boiling, fragrance agents typically have boiling points of about 250° C. or lower. The moderately volatile fragrance agents are those having boiling points of from about 250° C. to about 300° C. Many of the fragrance agents as discussed hereinafter, along with their odor characteristics, and their physical and chemical properties, such as boiling point and molecular weight, are given in "Perfume and Flavor Chemicals (Aroma Chemicals)," Steffen Arctander, published by the author, 1969, incorporated herein by reference.

Non-limiting examples of the highly volatile, low boiling, perfume agents include: anethole, benzaldehyde, benzyl acetate, benzyl alcohol, benzyl formate, iso-bornyl acetate, camphene, cis-citral (neral), citronellal, citronellol, citronellyl acetate, para-cymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl)cyclohexyl acetate). Some natural oils also contain large percentages of highly volatile fragrance agents. For example, lavandin contains as major components: linalool; linalyl acetate; geraniol; and citronellol. Lemon oil and orange terpenes both contain about 95% of d-limonene.

Non-limiting examples of moderately volatile perfume ingredients include: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Other known fragrance agents that have utility in the present technology can include one or more of: Acalea TBHQ, Allyl Amyl Glycolate, Alpha Terpineol, Ambrettolide, Amyl Cinnamic Aldehyde, Amyl Phenyl Acetate, Amyl Salicylate, Andrane, Anethole 21/22, Anethole USP, Aphermate, Apo Patchone, Bacdanol®, Benzyl Butyrate, Benzyl Propionate, Benzyl Salicylate, Bergamal, Beta Ionone Epoxide, Beta Naphthyl Iso-Butyl Ether, Bicyclononalactone, Bornafix®, Canthoxal, Cashmeran®, Cassiffix®, Cedrafix, Cedramber®, Cedryl Acetate, Celestolide, Cinnamalva, Citral Dimethyl Acetal, Citronalva, Citronellol 700 JAX, Citronellol 750, Citronellol 950, Citronellol Coeur, Citronellyl Acetate A, Citronellyl Acetate Coeur, Citronellyl Acetate Pure, Citronellyl Formate, Clarycet, Clonal, Coniferan, Cortex Aldehyde 50 Peomosa, Cyclabute, Cyclacet®, Cyclaprop®, Cyclemone A, Cyclobutanate, Cyclogalbaniff™, Cyclohexyl Ethyl Acetate, Cyclohexyl Ethyl Alcohol, Damascol 4, Decyl Methyl Ether, Delta Damascone, Dihydro Cyclacet, Dihydro Floralate, Dihydro Floralol, Dihydro Myrcenyl Acetate, Dihydro Terpineol, Dihydro Terpinyl Acetate, Dihydro Terpinyl Acetate DSA, Dimethyl Benzyl Carbinol, Dimethyl Benzyl Carbinyl Acetate, Dimethyl Benzyl Carbinyl Butyrate, Dimethyl Cyclormol, Dimethyl Octanol PQ, Dimethyl Phenyl Ethyl Carbinyl Acetate, Dimyrcetol, Diola, Dipentene 5100, Dulcinyl® Recrystalized, Ethyl Ortho Methoxy Benzoate, Ethyl Phenyl Glycidate, Fleuramone, Fleuranil, Floral Super, Floralate, Floralol, Floralozone, Floriffol, Fraistone, Fructone, Galaxolide® 50 BB, Galaxolide® 50 DEP, Galaxolide® 50 DPG, Galaxolide® 50 IPM, Galbanum Coeur, Galbascone, Galbascone High Alpha, Gelsone, Geraldehyde, Geraniol 5020, Geraniol 7030, Geraniol 980 Pure, Geraniol Coeur, Geranyl Acetate A, Geranyl Acetate Extra, Geranyl Acetate Pure, Grisalva, Guaiyl Acetate, Helional™, Herbac, Hexadecanolide, Hexylon, Hexenyl Salicylate, cis-3, Hexyl Acetate, Hexyl Cinnamic Aldehyde, Hexyl Salicylate, Hyacinth Body, Hyacinth Body No. 3, Hydratropic Aldehyde Dimethyl Acetal, Hydroxyol, Hypo-Lem, Indolarome, Indolene 50, Intreleven Aldehyde, Intreleven Aldehyde Special, Ionone 100%, Ionone Alpha, Ionone Alpha Beta Regular, Ionone Beta, Iso Amyl Butyrate, Iso Amyl Salicylate, Iso Bornyl Propionate, Iso Butyl Phenyl Acetate, Iso Butyl Quinoline, Iso Cyclemone E, Iso Cyclo Citral, Iso Cyclo Geraniol, Iso E Super®, Isoproxen, Jasmal, Jasmelia, Jessemal®, Kharismal®, Khusinil, Koavone®, Kohinool®, Labdanax, Lavonax, Lemsyn, Liffarome™, Lindenol™, Lymolene, Lyral®, Lyrame, Lyrame Super, Maritima, Meijiff™, Melafleur, Methyl Anthranilate, Methyl Cedryl Ketone Chinese, Methyl Cinnamic Aldehyde, alpha, Methyl Ionone Gamma A, Methyl Ionone Gamma Coeur, Methyl Ionone Gamma Extra, Methyl Ionone Gamma Pure, Methyl Ionone N, Methyl Lavender Ketone, Montaverdi®, Muguesia, Muguet Aldehyde 50, Muguet Aldehyde 50 BB, Musk Z4, Myrac Aldehyde, Myrcenol Super, Myrcenyl Acetate, Neoproxen, Nerol 800, Nerol 850, Nerol 900, Neryl Acetate JAX, New Car Smell fragrance (e.g. as containing castoreum and birch tar oil), Ocimene, Ocimenyl Acetate, Octacetal, Orange Flower Ether, Orivone, Orriniff™ 25% IPM, Oxaspirane, Ozofleur, Pamplefleur®, Peomosa, Phenafleur®, Phenoxanol®, Phenoxyethyl Iso Butyrate Phenoxyethyl Propionate, Phenyl Ethyl Acetate, Phenyl Ethyl Benzoate, Phenyl Ethyl Formate, Phenyl Ethyl Iso Butyrate, Phenyl Ethyl Phenyl Acetate, Phenyl Ethyl Salicylate, Piconia, Precyclemone B, Prenyl Acetate, Proflora, Pseudo Linalyl Acetate, Reseda Body, Rosalva, Rosamusk, Roseate, Rosemarel, Salicynalva, Sanjinol, Santaliff™, Spirodecane, Strawberiff®, Styralyl Propionate, Syvertal, Terpineol 900, Terpineol Alpha JAX, Terpineol Extra, Terpinolene 20, Terpinolene 90, Terpinolene 90 PQ, Terpinyl Acetate Extra, Terpinyl Acetate JAX, Tetrahydro Muguol®, Tetrahydro Muguol® Coeur, Tetrahydro Myrcenol, Tetrameran, Tobacarol, Triplal®, Trisamber®, Unipine® 60, Unipine® 85, Vandor® B, Vanoris, Verdol, Verdox™, Verdox™ HC, Verdural B Extra, Verdural Extra, Vertenex®, Vertenex® HC, Vertofix® Coeur, Vertoliff, Vertoliff Iso, Vigoflor Violiff, Vivaldie, Zenolide, 4,5-Dimethyl-2-ethyl-3-thiazoline, 6-Methyl Coumarin, Allyl Caproate, Asafoetida Oil English Distilled SAS, Black Pepper Oil, Buchu Sulfur Fractions, Butyric Acid, Cardamon Oil English Distilled SAS, Cassia Oil, Cassia Oil Redistilled, Cinnamon Bark Oil, Cinnamon Leaf Oil Cleaned, Clove Bud Oil English Distilled SAS, Clove Leaf Oil Redistilled, Oocal™, Cocoa Distillate (Nat.), Cocoa Essence Dark, Cocoa Essence White, Coffee Enhancer Base, Coffee Enhancer W/S, Coffee Extract, Coffee Extract Italian Roast M3881 Nat., Coffee Extract Nce him Nat., Coffee Extract Nce Iv Nat., Coriander Oil, Cyclodithalfarol-705, delta Decalactone, Dimethyl Sulfide, Dithione 865, Ethyl-2-Methyl Butyrate, Ethyl-3-Hydroxy Butyrate, Ethyl Butyrate, Ethyl Iso Butyrate, Ethyl Iso Valerate, Ethyl Oxanoate 369, Farnesene 1% PG/ETOH, Furfurrole 302, gamma-Decalactone, gamma-Hexylactone, gamma-Octalactone, gamma Dodecalactone, Ginger Oil Chinese, Ginger Oil Nigerian English Distilled SAS, Grapefruit Key, Grill Flavor O/S, Grill Flavor W/D, Heptan-2-One (Nat.), Hexene-3-One-4, Hexyl Acetate, Homo Cyclocitral, beta, Honey Distillate Nat., Ionone Beta, Iso Amyl Iso Valerate, Iso Butyl Caproate, Iso Butyl Furyl Propionate, Iso Fragarone-030, Iso Fragarone, 1% ETOH™, Isovaleric Acid, Juniperberry Oil English Distilled SAS, Ketone Mix, Kumarone™, Lemonless Lemon Key, Lime Oil Terpeneless, Linalool, Linalyl Acetate (Nat.), Mangone 5% ETOHT™, Methional, Methyl Butyric Acid (2), Methyl Ketones (Nat.), Methyl Oxycyclosulfide 719, Mint Oil Redist Yakima Type, Mint Type Oil Spec. Fractions, Mushroom Extract, Natural Flavor (99% Vanillin), Nat. Cocoa Butter Distillate, Nonan-2-One (Nat.), Nutmeg Oil East Indian, Octanal 35% (Nat.), Octen-4-one-2, Orange Oil 15X Decolorized M3706, Orange Oil 950 (10X), Orange Oil Terpeneless 2501, Oxaromate-884, Paradiff™ 0.01% ETOHGR, Paradiff™ 0.01% Grapefruit Oil, Peach Flavor Key, Phenyl Ethyl 2-Methyl Butyrate, Phenyl Ethyl Acetate, Phenyl Ethyl Alcohol, Phenyl Oxaromate-681, Pimento Berry Oil English Distilled SAS, Pimento Leaf Oil, Pimento Leaf Oil Cleaned, Pineapple Compound 15% ETOH GR, Pineapple Compound 15% PG, Popcorn Chemical, Propionic Acid, Raspberry Flavor Key, Raspberry Flavor Key, Raspberry Flavor Key, Robustone 1.0% ETOH™, Robustone™, Schinus Molle Oil, Sclareolide, Sesame Distillate Nat., Sinensals (Nat.), Starter Distillate 15X W/S, Strawberriff, Strawberry Base, Strawberry Flavor Key, Succinic Acid, Sulfurome-015, Sweetness Modifier, Tetrahydro Terrazine-014™, Thionol-935, Thionol-966, trans-2-Hexenal, Trimenal Acetate 399 1% ETOH™, Tropical Fruit Key Base, Tropical Fruit Key Base, Undecan-2-One (Nat.), Varamol-106 10% ETOH, Varamol-106 10% NEBM5 and Varamol-106 10% PG. These fragrance agents are commercially available form International Flavors and Fragrances Inc., (New York, N.Y., USA).

Other fragrance agents contemplated as being useful include botanical extracts that are capable of masking the malodor associated with bacteria, mold, viruses, mildew and germs and offensive chemical smells, such as those produced by cigarette smoke. Botanical extracts finding utility as fragrance agents in the present technology can include one or more plant extracts described in U.S. patent application Ser. No. 12/230,746, Pinney, V. R., published Jan. 8, 2009, which is hereby incorporated in its entirety.

Antimicrobial Agents

The odor neutralization agent can include one or more antimicrobial agents alone or in combination with one or more odor capture agents and fragrance agents. As used herein, an antimicrobial can include one or more of a biocide, a biostatic agent, a microbicidal agent, an antifungal agent, an antiviral agent, an antibacterial agent and combinations thereof. In some embodiments, if an odor neutralization agent includes an antimicrobial agent it will also include at least one of an odor capture agent and a fragrance agent.

In some embodiments, the antimicrobial agent can include a quaternary compound used alone or in conjunction with another odor neutralization agent. Non-limiting examples of useful quaternary compounds include: (1) benzalkonium chlorides and/or substituted benzalkonium chlorides such as commercially available Barquat® (available from Lonza), Maquat® (available from Mason), Variquat® (available from Witco/Sherex), and Hyamine® (available from Lonza); (2) di($C_6$-$C_{14}$) alkyl di short chain ($C_{1-4}$ alkyl and/or hydroxyalkyl) quarternary such as Bardac® products of Lonza, (3) N-(3-chloroallyl)hexaminium chlorides such as Dowicide® and Dowicil® available from Dow (Midland Mich., USA); (4) benzethonium chloride such as Hyamine® 1622 from Rohm & Haas; (5) methylbenzethonium chloride represented by Hyamine® 10X supplied by Rohm & Haas, and (6) cetylpyridinium chloride such as Cepacol chloride available from of Merrell Labs. Examples of the preferred dialkyl quaternary compounds are di($C_8$-$C_{12}$)dialkyl dimethyl ammonium chloride, such as didecyldimethylammonium chloride (Bardac 22), and dioctyldimethylammonium chloride (Bardac 2050).

Typical concentrations for antimicrobial effectiveness of these quaternary compounds in the odor remediation coating composition can range from about 0.001% to about 5%, preferably from about 0.005% to about 1%, more preferably from about 0.01% to about 0.2%, and even more preferably from about 0.03% to about 0.1%, by weight of the odor neutralization agent composition. The corresponding concentrations of the antimicrobial agents for use in an odor remediation coating can range from about 0.003% to about 2%, preferably from about 0.006% to about 1.2%, and more preferably from about 0.1% to about 0.8% by weight of the odor neutralization agent compositions.

Odor neutralization agents may be added in amounts ranging from 0.1-1, 5-10, 10-50 and 100-300, and 300-3000 mg/m$^2$ or more depending upon the strength and volatility of the odor neutralization agent. Known antimicrobial, biocidal or biostatic compounds would generally be applied at the lower end of this range but depending on their efficiency they can be added at one of the above listed ranges. An illustrative example of an antimicrobial agent includes one or more EPA registered biocides, for example, biocides such as Tektamer® products.

Typical carriers of these compounds can be oil based carriers, however, it is often desirable to use polar molecules such as alcohol and water as the carriers. The fragrance agents can be dispersed or dissolved in the carriers, and the carriers can be evaporated off after the dipping or spray application of the antimicrobial agent, fragrance agent or odor capture agent with the carrier. The ceramic coated heat exchanger component of claim 1, wherein said heat exchanger component further comprises an odor neutralizing agent delivery system selected to provide timed release of said agent.

In some embodiments, a longer lasting fragrance agent, odor capture agent or antimicrobial agent effect may be desired, it is possible to use carriers that do not evaporate but rather function as a microencapsulant and are left behind with the fragrance agent, odor capture agent or antimicrobial agents. In some embodiments, the ceramic coated heat exchanger component can also include an odor neutralizing agent delivery system to provide timed release of the odor neutralizing agent. The delivery system can include microencapsulants containing one or more odor neutralizing agents and a mechanical delivery device that provides the odor neutralizing agent from a storage container. The microencapsulant slowly allows small amounts of the one or more fragrance agent, odor capture agent or antimicrobial agents to bleed out over an extended time through them rather than being limited by diffusion out of the unique three dimensional nano and micro structure of the coating itself (i.e. the coating itself is a microencapsulant to some degree due to its unique structure).

Added microencapsulants may be simple oil emulsions in water (or inverse emulsions) or nanoparticles of solids such as ceramics, glasses, plastics such as polystyrene, or waxes which contain the fragrance, biocide or odor absorbing molecule trapped inside of them. These microencapsulants are small enough to lodge in the pores of the ceramic coating and may also be absorbed on the surface of the ceramic to allow a longer delivery of fragrance, biocide or odor absorbing molecules. The delivery system containing the microencapsulants can be tailored to a specific fragrance agent, odor capture agent and antimicrobial agent or combination thereof. The delivery system also includes a mechanical delivery device, for example, a spray, aerosol, liquid or solid applicator capable of delivering a fixed or variable quantity of encapsulated odor neutralizing agent known in the art. The microencapsulants can be stored in a storage container in proximate contact with the surface of the heat exchanger component, or alternatively, the storage container can be stored elsewhere and coupled to tubing that is operable for delivering the microencapsulants via a propulsion system, for example, forced fluid, vacuum or pressurized propellant.

In some embodiments, the present technology provides for additional components added to the heat exchanger components or to the structure of the automobile proximal to the heat exchanger component, for example, it is further advantageous to have a spray applicator having a pump, tubing and spray nozzle atomize more odor neutralizing agent e.g. fragrance agent, periodically onto and/or into the metal oxide ceramic coated heat exchanger component so that a predetermined or desired level of fragrance is maintained in the passenger cabin. In addition, the spray applicator can include a replaceable fragrance cartridge refill so that different a odor neutralizing agent, if desired can be swapped out by placing a new cartridge refill in the dispensing device and it would automatically change the fragrance (the fragrance pump subsystem would turn on and off in response to use of the blower that pushes air through the evaporator). In addition, automobile owner may want to put odor capture agents (such as cyclodextrins and other odor capture agents used for that purpose (known in the art commonly used today), rather than fragrances in the fragrance dispensing pump.

Ceramic Coatings

The method for preparing the metal oxide ceramic coatings of the present technology include metal oxide electrochemically deposited onto an aluminum containing surface of a heat exchanger component using an anodizing method described herein. The metal oxide coating, e.g. titanium oxide is then coated with an odor neutralization agent coated in an amount ranging from about 0.1 to about 1, from about 5 to about 10, from about 10 to about 50, from about 100 to about 300 and from about 300 to about 3,000 mg/m$^2$ absorbed onto and into the complex 3 dimensional structure of the electrochemical deposited ceramic coating. As can be seen from FIG. 1, a plurality of pores can be formed throughout the coating, including a plurality of pores formed on the surface of the ceramic coating. The pores afford a space for aggregation of the odor neutralization agent. The size of the pores can range from about 10 nm to about 3000 nm.

Antimicrobial Effect of the Ceramic Coating

In some embodiments, the metal oxide ceramic coating formed on the heat exchanger component can act as an antimicrobial agent when photocatalysed in the presence of short wavelength radiation; for example, ultraviolet (UV) light. In this alternative embodiment, the outer surface of the titanium oxide coated heat exchanger component is irradiated with an ultraviolet light or visible light having a wavelength, ranging from about 210-700 nm. The photocatalyst is energized with the ultraviolet light for facilitating a reaction between the odor molecules, oxygen and/or moisture on the surface of the heat exchanger and in the surrounding air. In some embodiments, surfaces of a heat exchanger component coated with titanium dioxide are exposed to UV light which can originate from UV light LEDs attached in proximity to the heat exchanger component. The ultraviolet light radiation source is placed in sufficient proximity with respect to the titanium dioxide coated heat exchanger surface such that the ultraviolet light being transmitted to the titanium dioxide coated heat exchanger surface activates the titanium dioxide coating and produces a peroxide when water is present thereby facilitating removal of the odor and killing any microbes in contact with the heat exchanger surface. Additionally, the titanium dioxide coated heat exchanger component may include sterilizing properties for facilitating preventing or reducing growth of viruses, bacteria and mold on the surfaces of the heat exchanger component.

The present technology will now be further described with reference to a number of examples, which are to be regarded solely as illustrative and not as restricting the scope of the present teachings.

EXAMPLES

Example 1

Comparative Sample 1

Methods for preparing a protective coating on heat exchanger parts using a non-chromate chemical conversion process are known in the art. For example, U.S. Pat. No. 7,353,863, Ser. No. 10/844,610 to Denso Corporation, issued Apr. 8, 2008 incorporated herein in its entirety, employs a non-chromate conversion process wherein the base body of the heat exchanger is pretreated with a etching agent comprising aqueous alkali solution and subsequent chemical conversion or a hydrophilicity-enhancing treatment to the etched base body. An aluminum base body of a heat exchanger which comprised a plurality of magnesium-containing aluminum alloy fins and tubes connected to each other by a vacuum brazing procedure, was brought into contact with an aqueous pretreatment liquid. The pretreated base body was subjected to an etching procedure using an aqueous alkaline solution in the manner as shown below and then to a desmutting (acid-washing) procedure in the manner as shown below. Thereafter, the etched base body is subjected to a non-chromate chemical conversion treatment and then to a hydrophilicity-enhancing treatment in a manner as shown below.

Steps For Preparing A Non-Chromate Conversion Coating of Comparative Sample 1.

(1) Desmutting (Acid-Washing) Treatment. In Comparative sample 1 an aluminum heat exchanger base body for example an RS Evaporator manufactured by Denso, Mich., USA (having a fin with a liner made with BA4343-400 series aluminum, a core made from DA3913S-300 series aluminum and a tube made from DA1197 aluminum) is immersed in an aqueous solution of an acid (0.15-0.3% $HNO_3$) at room temperature for 10 seconds, to remove the smut from the base body surfaces and then rinsed with water.

(2) Chemical Conversion Treatment. The desmutted base body of the heat exchanger component of Comparative Sample 1 is then immersed in a chemical conversion treatment liquid comprising 30% fluorozirconic acid and 1% hydrofluoric acid in water and maintained at a temperature of 50° C., for 60 seconds, to thereby form a zirconium chemical conversion coating on the base body surfaces.

(3) Hydrophilicity-Enhancing Treatment. In Comparative sample 1, the chemical conversion-treated base body of the heat exchanger is rinsed with water and then immersed in a foaming hydrophilicity-enhancing treatment liquid of a zircon-type organic-inorganic composite agent, for example, Surfalcoat™ 2400 (Nippon Paint Kabushiki Kaisha (Nippon Paint Co., LTD, Japan)) and maintained at a temperature of 25° C., for 30 seconds. The base body is taken out from the treatment liquid, dripped to remove an excessive portion of the treatment liquid adhered to the base body surfaces, and cured in a hot air-circulating oven set to a temperature of 150° C. for 2-20 minutes, to form a hydrophilic coating on the base body surfaces.

Procedure for Preparation of a Heat Exchanger Using Plasma Electrochemical Deposition of Titanium Oxide (A) Hot Water Wash/Degreasing Of Heat Exchanger;

(B) Plasma Electrochemical Deposition Using Anodizing Solution Comprising Titanium Metal Salts;

(C) Air Drying;

(D) Coating With An Odor Neutralization Agent; and (E) Rinse and/or Air Drying (optional—odor neutralizing agent may be dried in place eliminating step E) and The heat exchanger component, an RS Evaporator, manufactured by Denso, Mich., USA (having a fin with a liner made from BA4343-400 series aluminum, a core made from DA3913S-300 series aluminum and a tube made from DA1197 aluminum) was immersed in a 6% Alodine ECC 9000, an aqueous electrolytic solution commercially available from Henkel Corporation, and described by the manufacturer as containing fluorotitanic acid, a phosphorus containing composition and various fluoride and titanium compounds. Treatment bath pH was 2.7. The heat exchanger was connected as the anode in the electrolytic cell of the solution for 3 minutes to 20 minutes thereby depositing 1 g-10 g/m$^2$ of largely titania and titanium phosphate. The core was removed from the electrolyte solution, rinsed with deionized water and allowed to dry. Odor neutralization agents were added at the ranges above. For example, 3 milliliters of oil of peppermint was added to a one liter of 25% solution of ethanol and water and the heat exchanger was immersed in this admixture for 30 seconds and then dried in air. Other fragrance agents tested were orange extract, lemon extract and commercially available fragrances of cherry, as well as an oatmeal/milk/honey scent. The fragrance agents were applied according to the procedure for the peppermint scent, and retained their scent on the coating after being air dried.

Three samples were coated with DC pulsed current at peak voltages of 450 volts and average voltage of 136 volts. A 3 micron thick coating resulted from 10 minutes treatment, a 5 micron thick coating resulted from 15 minutes treatment and a 10 micron thick coating resulted from 20 minutes treatment.

Test Sample 1 used in the tests and evaluations below was produced according to the above described experimental procedure with a three micron thick coating and no odor remediation coating treatment.

Tests and Evaluations

For testing and evaluating the corrosion resistance of the coatings obtained using Comparative sample 1 using a non-chromate liquid conversion process and test sample 1 using plasma electrochemical deposition, the same heat exchanger component was used in each of the various tests.

(i) Cooling Performance

An evaporator produced in accordance with Comparative sample 1 and Test sample 1 are filled with cooling fluids. The evaporators are operating at an air flow rate of 100-1000 m$^3$/hr or higher. Measurements of cooling performance are made at various points of air flow within the evaporator. Cooling performance results are expressed as W. Results are summarized in Table 1.

(ii) Contact Angle (Hydrophilic Ability/Water Shedding)

A specimen (fin) from an evaporator coated with the process described in Comparative sample 1 having a coating thickness of 8-9 microns and a fin coated in the manner described in Test sample 1 having a titanium oxide coating of 3 microns was immersed in a purified water stream flowing at a flow rate of 0.5 liter/min. for 72 hours. The contact angle of the fin surface with water for each fin specimen was measured by using a contact angle meter (model: CA-X type, made by KYOWA KAIMEN-KA-GAKU K.K., Japan). The number of the testing points on the fin surface was twelve. The hydrophilicity of the fin surface was represented by the resultant highest and lowest contact angles. Results are summarized in Table 1.

(iii) Burst (Durability)

This test measures the durability of the coated heat exchanger component having a protective coating prepared in accordance with a non-chromate conversion coating method of Comparative sample 1 or by plasma electrochemical deposition as described in Test sample 1. An evaporator prepared in accordance with the method of Comparative sample 1 and an evaporator prepared in accordance with the method of Test sample 1 are each filled with oil, then each evaporator is pressurized to the pressure resistance specification (17 kgf/cm$^2$). The evaporators are monitored and no deformation or leakage is permitted. The evaporators are further pressurized until the evaporator bursts. Burst resistance must exceed 30 kgf/cm$^2$. The applied corrosion resistance coatings using the methods of Comparative sample 1 and the method of the present technology (Test sample 1) can be directly compared and evaluated by the burst (durability) test. Results are summarized in Table 1.

(iv) White Rust Resistance (Corrosion Resistance)

A fin portion of an aluminum alloy heat exchanger is subjected to a salt spray test using an aqueous corrosion salt solution comprising 50 g/liter of sodium chloride in water for a testing period of 240 hours. Then, the amount of white rust (aluminum oxide) on the fin is directly quantified by placing a 5 kg weight onto one side of an evaporator coated with a protective coating using the methods described for Comparative sample 1 above and a second evaporator prepared using the methods described for Test sample 1. The weighted evaporator's bottom surface (not attached to the weight) having been exposed to 240 hours of salt spray is then dropped from a height of 80 mm onto a substrate operable to collect any white rust present on the surface of the contacted evaporator which has fallen off. Using this method of white rust quantification, a poorer corrosion resistance coating will develop a greater quantity of white rust and when dropped onto a collection substrate will deposit a greater amount of white rust compared to a better corrosion resistance coating. Hence, the amount of white rust collected on the substrate inversely correlates with the corrosion resistance capacity of the coating on the tested heat exchanger component after salt spray exposure. Results are summarized in Table 1.

(v) Mist Spray (Corrosion Resistance Equivalent to ASTM-B117-03)

The mist spray corrosion resistance test can be used to compare the corrosion resistance of the coatings of (Comparative sample 1) and (Test sample 1). The present test is broadly equivalent to the American Society for Testing and Materials (ASTM) ASTM B117-03 test. A chamber is prepared having mist sprayers providing a mist comprising Cl$^-$ ions at 6060 ppm, $SO_4^{2-}$ at 200 ppm and $Cu^{2+}$ at 10 ppm. The salt spray is propelled onto the heat exchanger components (heat exchangers) prepared in accordance with Comparative sample 1 and a heat exchanger prepared in accordance with Test sample 1. The humidity of the interior of the chamber is approximately 95% or greater and the interior of the chamber was set to a temperature of 50° C. A scribed vertical line was placed on a surface of each heat exchanger and then exposed to the salt mist spray for a period in excess of 10,000 hours. Periodic examination of the two heat exchangers were conducted to measure the presence and extent of surface corrosion and/or rust extending from the scribed line. FIG. 2 shows the results on a heat exchanger component showing effectively no corrosion along the scribed line after at least 4000 hrs of exposure to the salt spray. The results are summarized in Table 1.

(vi) Odor Adhesion

Without wishing to be bound by any one particular theory, it is believed that one of the most offensive and noxious odors capable of fouling a heat exchanger after many hours of exposure is cigarette smoke. The inventors have unexpectedly found a surface coating comprising a metal oxide ceramic coating coated with an odor remediation coating for a heat exchanger component, for example an evaporator, which remediates the odor of cigarette smoke.

A cigarette smoke collection and testing device was prepared to conduct the present odor adhesion test. The test is conducted in a sealed chamber having an air inlet streaming air at and an opening in the proximity of the flow of streaming air for introducing cigarette smoke into the chamber. The cigarette was consumed at approximately the same rate as typically consumed by an average smoker providing a flow of cigarette smoke to the surface of the heat exchanger component. The cigarette smoke was then channeled to a surface of an evaporator prepared in accordance with Comparative Sample 1 and Test sample 1. The amount of cigarette odor adhered to the exposed surface of the evaporator was assessed by manually smelling the exposed surface and rating the odor determined as 0.0 being no odor to 1.0 as being the strongest odor. Two parameters were determined using the assessment scale, one for adverseness (noxiousness (quality)) and one for strength (quantity). The results are summarized in Table 1.

TABLE 1

Surface Treatment Test Results of Heat Exchanger Components Coated Using the Methods Described in Comparative sample 1 and Test sample 1.

| Evaluation Test | Comparative Sample 1 (Non-chromate conversion coatings) | Test sample 1 Electrochemical Deposition metal oxide coatings | Advantage Test Sample 1 over Comparative sample 1 |
|---|---|---|---|
| Cooling performance (W) | 3472.47 | 3512.93 | 5% improvement |
| Contact Angle (Hydrophilic ability/Water shedding) Range in degrees | 25-35 | 10-23 | 20% improvement |
| Burst (Durability) in kgf/cm$^2$ | 56 | 65 | 15% improvement |
| White Rust Resistance in g/m$^2$ | 0.3-0.5 | ~0 | 100% improvement |
| Mist Spray (Corrosion resistance) (Indication of corrosion at Hrs) | 850 | >10,000 | >1000% improvement |
| Odor Adhesion Scale 0.0 (Best)-1.0 (Worst) | Averseness = 1.0 Strength = 0.9 | Averseness = 0.5 Strength = 0.45 | 50% improvement |

The results from the comparative and test sample analysis of corrosion resistance performance above appears to indicate that the present technology employing plasma electrochemical deposition provides coatings having significant improvements in corrosion resistance over other coating methods used in the field of automotive heat exchanger corrosion protection. In addition to the reduction in toxic and harmful etching, cleaning and resin chemicals, the metal oxide odor remediation coatings of the present technology are superior in performance warranting against corrosion when compared to non-chromate chemical conversion coatings. The materials and processes used in the present technology have a reduced impact on the environment and are generally less expensive, by an order of magnitude. Furthermore, the methods for making heat exchanger components of the present technology do not require heat intensive curing or annealing steps that add time and resources to the production requirements for making these heat exchanger components. Most of the steps involved in making the present heat exchanger components having metal oxide ceramic coatings can be performed at ambient temperatures. The present methods also reduce the use of volatile organic compounds by 100% as compared to non-chromate conversion coating methods.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A ceramic coated heat exchanger component comprising:
   (A) a heat exchanger component having an aluminum surface;
   (B) a ceramic coating disposed on at least a portion of said aluminum surface, said ceramic coating comprising titanium oxide and, optionally, further comprising a metal oxide ceramic selected from the group consisting of zirconium oxide, hafnium oxide, tin oxide, niobium oxide, vanadium oxide, molybdenum oxide, manganese oxide, tungsten oxide and combinations thereof, said ceramic coating having a thickness of from 1 to 20 microns and said ceramic coating having a plurality of pores having a diameter of from 10 to 3000 nanometers on an exterior surface of said ceramic coating; and
   (C) an odor neutralization agent coating bound onto said exterior surface of said ceramic coating, said odor neutralization agent coating having a composition other than that of a metal oxide ceramic coating, and wherein at least a portion of said plurality of pores contain said odor neutralization agent coating.

2. The ceramic coated heat exchanger component of claim 1, wherein said heat exchanger component comprises aluminum, an aluminum alloy, magnesium, manganese, zirconium, tin, tungsten, iron, nickel, titanium, carbon, niobium, vanadium, copper, brass, silicon or combinations thereof.

3. The ceramic coated heat exchanger component of claim 1, wherein said ceramic coating has a thickness ranging from 1 micron to about 5 microns.

4. The ceramic coated heat exchanger component of claim 1, wherein said odor neutralization agent coating comprises an odor capture agent, a fragrance agent, an antimicrobial agent or combinations thereof.

5. An automobile comprising a heat exchanger component of claim 1.

6. The ceramic coated heat exchanger component of claim 1, wherein said odor neutralizing agent coating further comprises a non-evaporating carrier to provide timed release of said agent.

7. The ceramic coated heat exchanger component of claim 1, wherein said odor neutralizing agent coating comprises a cyclodextrin.

8. The ceramic coated heat exchanger component of claim 1, wherein said ceramic coating has been photocatalysed by exposure to ultraviolet light or visible light having a wavelength ranging from about 200 to about 700 nm thereby providing said ceramic coating with antimicrobial activity.

9. A coated heat exchanger component comprising:
  a. a heat exchanger component having an aluminum surface;
  b. a ceramic coating comprising at least 50 wt % titanium oxide disposed at least partially on said aluminum surface, said titanium oxide ceramic coating having a component contact surface and an exterior surface; said ceramic coating applied to said aluminum surface using plasma electrochemical deposition, and said ceramic exterior surface having a plurality of pores having a pore diameter of from 10 to 3000 nanometers, said ceramic coating having a thickness of from 1 to 20 microns; and
  c. an odor neutralizing agent coating having a composition other than said titanium oxide ceramic coating, said odor neutralization agent coating bound onto said titanium oxide ceramic coating exterior surface and at least partially in said plurality of pores.

* * * * *

UNITED STATES PATENT AND TRADEMARK OFFICE
CERTIFICATE OF CORRECTION

PATENT NO. : 9,701,177 B2
APPLICATION NO. : 12/417433
DATED : July 11, 2017
INVENTOR(S) : Chris McDermott et al.

It is certified that error appears in the above-identified patent and that said Letters Patent is hereby corrected as shown below:

In the Specification

Column 19, Line 35: Change "Hexylon" to -- Hexalon --.

Column 20, Line 15: Change "Oocal™" to -- Cocal™ --.

Column 20, Line 19: Change "him" to -- liim --.

Column 20, Line 25: Change "Hexylactone" to -- Hexalactone --.

Column 20, Line 35: Change "ETOHT™" to -- ETOH™ --.

Signed and Sealed this
Twenty-seventh Day of March, 2018

Andrei Iancu
*Director of the United States Patent and Trademark Office*